(12) United States Patent
Kramer et al.

(10) Patent No.: US 6,683,183 B2
(45) Date of Patent: Jan. 27, 2004

(54) PYRIDOTRIAZINES AND PYRIDOPYRIDAZINES

(75) Inventors: James Bernard Kramer, Sylvania, OH (US); Howard Daniel Hollis Showalter, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/970,107

(22) Filed: Oct. 3, 2001

(65) Prior Publication Data

US 2002/0061865 A1 May 23, 2002

Related U.S. Application Data

(60) Provisional application No. 60/237,601, filed on Oct. 3, 2000.

(51) Int. Cl.$^7$ ..................... C07D 487/04; A61K 31/53; A61P 35/00
(52) U.S. Cl. ..................... 544/184; 544/236; 514/243; 514/248
(58) Field of Search ................ 544/184, 236; 514/243, 248

(56) References Cited

PUBLICATIONS

R.T. Abraham, et al., "Cellular Effects of Olomoucine, and Inhibitor of Cyclin–dependent Kinases" Biol. Cell, 1995, pp 105–120, vol. 83.

D.W. Fry, et al., "Inhbitors of Cyclin–dependent Kinases as Therapeutic Agents for the Treatment of Cancer", Curr. Opin. Oncol. Endo. Metabol. Invest. Drugs, 2000, pp 40–59, vol. 2, No. 1.

G. Kaur, et al., "Growth Inhibition with Resversible Cell Cycle Arrest of Carcinoma Cells by Flavone L86–8275", J. Natl. Can. Inst., Nov. 18, 1992, pp 1736–1740, vol. 84, No. 22.

L. Meijer, "Chemical Inhibitors of Cyclin–dependent Kinases", Prog. Cell Cycl. Res., 1995, pp 351–363, vol. 1.

H. H. Sedlacek, et al., "Flavopiridol (L86 8275; NSC 649890), a New Kinase Inhibitor for Tumor Therapy", Inter. J. Oncol., 1996, pp 1143–1168, vol. 9.

L. Sun, et al., "Inhibition of Tumor Angiogenesis by Synthetic Receptor Tyrosine Kinase Inhibitors", DDT, Aug. 8, 2000, pp 344–353, vol. 5, No. 8.

J. Vesely, et al., "Inhibition of Cyclin–Dependent Kinases by Purine Analogues", eUR. j. bIOCEHM., 1994, pp 771–786, vol. 224.

*Primary Examiner*—Richard L Raymond
*Assistant Examiner*—Venkataraman Balasubramanian
(74) *Attorney, Agent, or Firm*—Charles W. Ashbrook; Rosanne Goodman

(57) ABSTRACT

This invention relates to bicyclic heterocycles that inhibit cyclin-dependent kinase or tyrosine kinase enzymes, or both, and as such are useful to treat cell proliferative disorders such as angiogenesis, atherosclerosis, restenosis, and cancer as well as immunological disorders such as asthma, rheumatoid arthritis, autoimmune diabetes, and graft rejection associated with transplant surgery in mammals.

23 Claims, No Drawings

PYRIDOTRIAZINES AND PYRIDOPYRIDAZINES

This application claims priority to U.S. patent application Ser. No. 60/237,601 filed Oct. 3, 2000.

FIELD OF THE INVENTION

This invention relates to bicyclic heterocycles that inhibit cyclin-dependent kinase or tyrosine kinase enzymes, or both, and as such are useful to treat cell proliferative disorders such as angiogenesis, atherosclerosis, restenosis, and cancer as well as immunological disorders such as asthma, rheumatoid arthritis, autoimmune diabetes, and graft rejection associated with transplant surgery in mammals.

SUMMARY OF THE RELATED ART

Tyrosine kinases are a class of enzymes that catalyze the transfer of the terminal phosphate of adenosine triphosphate (ATP) to tyrosine residues on protein substrates. Tyrosine kinases are an integral part of growth factor receptors and are essential for the propagation of growth factor signal transduction leading to cellular proliferation, differentiation, and migration. Growth factor receptors are also known as receptor tyrosine kinases (RTKs). The aberrant regulation of growth factors or their cognate receptors plays a critical role in the progression of proliferative diseases. For example, fibroblast growth factor (FGF) and vascular endothelial growth factor (VEGF) have been implicated as important mediators of tumor promoted angiogenesis (Sun L. and McMahon G., "Inhibition of Tumor Angiogenesis by Synthetic Receptor Tyrosine Kinase Inhibitors," *Drug Discovery Today*, 2000;5(8):344–353). Solid tumors are dependent upon the formation of new blood vessels from preexisting vessels (angiogenesis) to nourish their growth and to provide a conduit for metastases. Accordingly, inhibitors of the FGF and VEGF RTKs, as well as other tyrosine kinases, are useful agents for the prevention and treatment of proliferative diseases dependent on these enzymes.

Cell cycle kinases are naturally occurring enzymes involved in regulation of the cell cycle (Meijer L., "Chemical Inhibitors of Cyclin-Dependent Kinases," *Progress in Cell Cycle Research*, 1995;1:351–363). Typical enzymes include the cyclin-dependent kinases (cdk) cdk1 (also known as cdc2), cdk2, cdk4, cdk5, cdk6, and wee-1 kinase. Increased activity or temporally abnormal activation of these kinases has been shown to result in development of human tumors and other proliferative disorders such as restenosis (Fry D. and Garrett M., "Inhibitors of Cyclin-Dependent Kinases as Therapeutic Agents for the Treatment of Cancer," *Current Opinion in Oncologic, Endocrine, and Metabolic Investigational Drugs*, 2000;2(1):40–59). Compounds that inhibit cdks, either by blocking the interaction between a cyclin and its kinase partner, or by binding to and inactivating the kinase, cause inhibition of cell proliferation, and are thus useful for treating tumors or other abnormally proliferating cells.

Several compounds that inhibit cdks have demonstrated both preclinical and clinical anti-tumor activity. For example, flavopiridol is a flavonoid that has been shown to be a potent inhibitor of several types of breast and lung cancer cells (Kaur, et al., *J. Natl. Cancer Inst.*, 1992;84:1736–1740; *Int. J. Oncol.*, 1996;9:1143–1168). The compound has been shown to inhibit cdk2 and cdk4. Olomoucine [2-(hydroxyethylamine)-6-benzylamine-9-methylpurine] is a potent inhibitor of cdk2 and cdk5 (Vesely, et al., *Eur. J. Biochem.*, 1994;224:771–786), and has been shown to inhibit proliferation of approximately 60 different human tumor cell lines used by the National Cancer Institute (NCI) to screen for new cancer therapies (Abraham, et al., *Biology of the Cell*, 1995;83:105–120).

Despite the progress that has been made, the search continues for small molecular weight compounds that are orally bioavailable and useful for treating a wide variety of human tumors and other proliferative disorders such as restenosis, angiogenesis, diabetic retinopathy, psoriasis, surgical adhesions, macular degeneration, and atherosclerosis and immunological disorders such as asthma, rheumatoid arthritis, autoimmune diabetes, and graft rejection associated with transplant surgery in mammals.

SUMMARY OF THE INVENTION

This invention provides bicyclic heterocycles that are useful for treating cell proliferative disorders, such as cancer, atherosclerosis, restenosis, angiogenesis, diabetic retinopathy, psoriasis, and endometriosis and immunological disorders. These pyridotriazine and pyridopyridazine analogs are inhibitors of tyrosine kinases and cyclin-dependent kinases (cdks). The disclosed compounds are readily synthesized and can be administered by a variety of routes, including orally and parenterally.

The compounds of the invention are members of the class of compounds of Formula I:

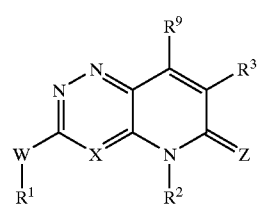

and the pharmaceutically acceptable salts thereof, wherein:

W is NH, S, SO, or $SO_2$;

X is N or CH;

Z is O, S, or $NR^{10}$;

Each of $R^1$, $R^2$, and $R^{10}$ are independently selected from the group consisting of H, $(CH_2)_n Ar$, $COR^4$, $(CH_2)_n C_3$–$C_5$ heteroaryl, $(CH_2)_n C_3$–$C_5$ heterocyclyl, $C_1$–$C_{10}$ alkyl, $C_3$–$C_{10}$ cycloalkyl, $C_2$–$C_{10}$ alkenyl, and $C_2$–$C_{10}$ alkynyl, wherein n is 0, 1, 2, or 3, and the $(CH_2)_n Ar$, $(CH_2)_n$heteroaryl, alkyl, cycloalkyl, alkenyl, and alkynyl groups are optionally substituted by up to 5 groups selected from $NR^5R^6$, $N(O)R^5R^6$, $NR^5R^6R^7Y$, $C_1$–$C_4$ alkyl, phenyl, substituted phenyl, $(CH_2)_n$heteroaryl, hydroxy, $C_1$–$C_4$ alkoxy, phenoxy, thiol, $C_1$–$C_4$ thioalkyl, halo, $COR^5$, $CO_2R^5$, $CONR^5R^6$, $SO_2NR^5R^6$, $SO_3R^5$, $PO_3R^5$, $C_1$–$C_5$ aldehyde, nitrile, nitro, $C_3$–$C_6$ heteroaryloxy, $T(CH_2)_m QR^4$,

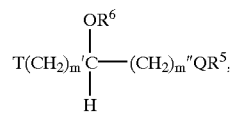

$C(O)T(CH_2)_m QR^5$, $NHC(O)T(CH_2)_m QR^5$, $T(CH_2)_m C(O)$ $NR^5NR^6$, and $T(CH_2)_m CO_2R^5$ wherein each of m, m', and m" is independently 1–6, T is O, S, $NR^7$, $N(O)R^7$, $NR^7R^8Y$, or $CR^7R^{11}$, and Q is O, S, $NR^{11}$, $N(O)R^{11}$, or $NR^{11}R^8Y$;

$R^3$ and $R^9$ have the meanings of $R^2$, wherein $R^2$ is as defined above, as well as OH, $NR^{12}R^{13}$, $COOR^{12}$, $OR^{12}$, $CONR^{12}R^{13}$, $SO_2NR^{12}R^{13}$, $SO_3R^{12}$, $PO_3R^{12}$, $T'(CH_2)_mQ'R^4$,

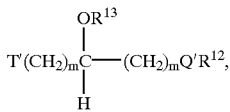

wherein T' and Q' are as defined above for T and Q, respectively;

$R^4$, $R^5$, $R^6$, $R^7$, $R^{11}$, $R^{12}$, $R^{13}$, $R^{14}$, and $R^{15}$ are each independently selected from the group consisting of hydrogen, $C_1$–$C_6$ alkyl, substituted $C_1$–$C_6$ alkyl, $C_2$–$C_6$ alkenyl, $C_2$–$C_6$ alkynyl, $N(C_1$–$C_6$alkyl$)_{1\ or\ 2}$, $(CH_2)_nAr$, $C_3$–$C_{10}$ cycloalkyl, $C_3$–$C_6$ heterocyclyl, and $C_3$–$C_6$ heteroaryl, or $R^5$ and $R^6$, or $R^7$ and $R^8$, or $R^{12}$ and $R^{13}$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, sulfur, and substituted sulfur; or when $R^5$ and $R^6$, or $R^7$ and $R^8$, or $R^{12}$ and $R^{13}$ together with the nitrogen to which they are attached form a ring, said ring is optionally substituted by 1 to 3 groups selected from $OR^{14}$, $NR^{14}R^{15}$, $(CH_2)_mOR^{14}$, $(CH_2)_mNR^{14}R^{15}$, T"—$(CH_2)_mQ"R^{14}$, CO—T"—$(CH_2)_mQ"R^{14}$, $NH(CO)T"(CH_2)_mQ"R^{14}$, T"—$(CH_2)_mCO_2R^{14}$, or $T"(CH_2)_mCONR^{14}R^{15}$; wherein T" and Q" are as defined above for T and Q;

$R^8$ is $C_1$–$C_6$ alkyl or $C_3$–$C_6$ cycloallyl; and

Y is a halo counter-ion.

This invention also provides pharmaceutical formulations and pharmaceutical compositions comprising a compound of Formula I together with a pharmaceutically acceptable carrier, diluent, or excipient therefor.

Compounds within the scope of the present invention are inhibitors of a wide variety of kinases like the cyclin-dependent kinases such as cdk2, cdc2, and cdk4 and especially of growth factor mediated tyrosine kinases including those of platelet-derived growth factor (PDGF), fibroblast growth factor (FGF), vascular endothelial growth factor (VEGF), and epidermal growth factor (EGF), as well as non-receptor tyrosine kinases such as a transforming gene of the Rous sarcoma retrovirus (Src) family, c-Src and Lck.

As inhibitors of cyclin-dependent, as well as growth factor-mediated and non-receptor tyrosine kinases, the disclosed compounds are useful in controlling proliferative disorders such as cancer, psoriasis, diabetic retinopathy, angiogenesis, vascular smooth muscle cell proliferation, vascular smooth muscle cell proliferation associated with atherosclerosis, diabetic retinopathy, angiogenesis, postsurgical vascular stenosis and restenosis, and immunological disorders such as asthma, rheumatoid arthritis, autoimmune diabetes, and graft rejection associated with transplant surgery in mammals. As such, the present invention provides a method for treating any of the disorders mentioned above in a mammal, said method comprising administering to said mammal a therapeutically effective amount of a compound of Formula I or of a pharmaceutical composition comprising a compound of Formula I.

A further embodiment of this invention is a method of treating subjects suffering from diseases caused by cellular proliferation. The method entails inhibiting proliferation of tumorigenic cells of epithelial origin and vascular smooth muscle proliferation, and/or cellular migration by administering a therapeutically effective amount of a compound of Formula I to a subject in need of treatment.

A further embodiment of this invention is a method of treating subjects suffering from disorders of the immune system. The method entails inhibiting protein kinases, specifically T-cell tyrosine kinase p56$^{lck}$ by administering a therapeutically effective amount of a compound of Formula I to a subject in need of treatment.

Another embodiment of this invention is a method for inhibiting an enzyme selected from cyclin-dependent kinases, growth factor-mediated kinases, and non-receptor tyrosine kinases, said method comprising exposing said enzyme, in vivo or in vitro, to an inhibiting amount of a compound of Formula I or a metabolite thereof.

A further embodiment of this invention is a method for treating immunological disorders associated with T-cell tyrosine kinases or with B-cell tyrosine kinases in a mammal, said method comprising administering to said mammal a therapeutically effective amount of a compound of Formula I.

A further embodiment of this invention is a method for inhibiting a wee-1 kinase, said method comprising exposing said enzyme, in vivo or in vitro, to an inhibiting amount of a compound of Formula I or a metabolite thereof.

A further embodiment of this invention is a method of treating subjects suffering from diseases caused by DNA tumor viruses such as herpes viruses.

In addition, the present invention provides the use of a compound of Formula I, or a pharmaceutically acceptable salt thereof for the manufacture of a medicament for treating or preventing any of the disorders mentioned above.

Furthermore, the present invention provides the use of a compound of Formula I, or a pharmaceutically acceptable salt thereof for treating or preventing any of the disorders mentioned above.

DETAILED DESCRIPTION OF THE INVENTION

The invention features compounds that inhibit a variety of kinases, thus the compounds are useful agents for treating subjects suffering from diseases caused by abnormal cell proliferation and diseases of the immune system. Compounds within the scope of the present invention are inhibitors of a wide variety of kinases like the cyclin-dependent kinases such as cdk2, cdc2, and cdk4 and especially of growth factor mediated tyrosine kinases including those of platelet-derived growth factor (PDGF), fibroblast growth factor (FGF), vascular endothelial growth factor (VEGF), and epidermal growth factor (EGF), as well as non-receptor tyrosine kinases such as a transforming gene of the Rous sarcoma retrovirus (Src) family, c-Src and Lck. As inhibitors of cyclin-dependent, as well as growth factor-mediated and non-receptor tyrosine kinases, the compounds of the instant invention are useful in controlling proliferative disorders such as cancer, psoriasis, vascular smooth muscle cell proliferation associated with atherosclerosis, diabetic retinopathy and angiogenesis, postsurgical vascular stenosis and restenosis, and immunological disorders such as asthma, rheumatoid arthritis, autoimmune diabetes, and graft rejection associated with transplant surgery in mammals.

The present invention provides a compound of Formula I

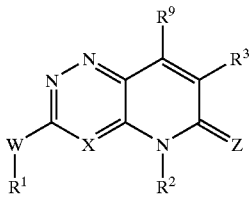

I and the pharmaceutically acceptable salts thereof, wherein:
W is NH, S, SO, or $SO_2$;
X is N or CH;
Z is O, S, or $NR^{10}$;
Each of $R^1$, $R^2$, and $R^{10}$ are independently selected from the group consisting of H, $(CH_2)_n$Ar, $COR^4$, $(CH_2)_n$ $C_{3-C5}$ heteroaryl, $(CH_2)_n$ $C_3$–$C_6$ heterocyclyl, $C_1$–$C_{10}$ alkyl, $C_3$–$C_{10}$ cycloalkyl, $C_2$–$C_{10}$ alkenyl, and $C_2$–$C_{10}$ alkynyl, wherein n is 0–6 and the $(CH_2)_n$Ar, $(CH_2)_n$heteroaryl, heterocyclyl, alkyl, cycloalkyl, alkenyl, and alkynyl groups are optionally substituted by up to 5 groups selected from $NR^5R^6$, $N(O)R^5R^6$, $NR^5R^6R^7Y$, $C_1$–$C_4$ alkyl, phenyl, substituted phenyl, $(CH_2)_n$heteroaryl, hydroxy, $C_1$–$C_4$ alkoxy, phenoxy, thiol, $C_1$–$C_4$ thioalkyl, halo, $COR^5$, $CO_2R^5$, $CONR^5R^6$, $SO_2NR^5R^6$, $SO_2R^5$, $SO_3R^5$, $PO_3R^5$, $C_1$–$C_5$ aldehyde, nitrile, nitro, $C_3$–$C_6$ heteroaryloxy, $T(CH_2)_mQR^4$,

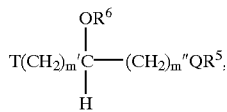

$C(O)T(CH_2)_mQR^5$, $NHC(O)T(CH_2)_mQR^5$, $T(CH_2)_mC(O)NR^5NR^6$, and $T(CH_2)_mCO_2R^5$, wherein each of m, m' and m" is independently 1–6, T is O, S, $NR^7$, $N(O)R^7$, $NR^7R^8Y$, or $CR^7R^{11}$, and Q is O, S, $NR^{11}$, $N(O)R^{11}$, or $NR^{11}$ $R^8Y$;

$R^3$ and $R^9$ are each OH, $NR^{12}R^{13}$, $COOR^{12}$, $OR^{12}$, $CONR^{12}R^{13}$, $(CH_2)_nCOR^{12}$, $(CH_2)_nCOOR^{12}$, halo, $SO_2NR^{12}R^{13}$, $SO_3R^{12}$, $PO_3R^{12}$, $T'(CH_2)_mQ'R^4$,

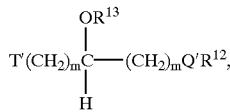

or as defined above for $R^2$,
wherein T' and Q' are as defined above for T and Q, respectively;
$R^4$, $R^5$, $R^6$, $R^7$, $R^{11}$, $R^{12}$, $R^{13}$, $R^{14}$, and $R^{15}$ are each independently selected from the group consisting of hydrogen, $C_1$–$C_6$ alkyl, substituted $C_1$–$C_6$ alkyl, $C_2$–$C_6$ alkenyl, $C_2$–$C_6$ alkynyl, $N(C_1$–$C_6$alkyl$)_{1\ or\ 2}$, $(CH_2)_n$Ar, $C_3$–$C_{10}$ cycloalkyl, $C_3$–$C_6$ heterocyclyl, and $C_3$–$C_6$ heteroaryl, or $R^5$ and $R^6$, or $R^7$ and $R^8$, or $R^{12}$ and $R^{13}$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, sulfur, and substituted sulfur; or when $R^5$ and $R^6$, or $R^7$ and $R^8$, or $R^{12}$ and $R^{13}$ together with the nitrogen to which they are attached form a ring, said ring is optionally substituted by 1 to 3 groups selected from $C_1$–$C_3$ alkyl, OH, $OR^{14}$, $NR^{14}R^{15}$, $(CH_2)_m$ $OR^{14}$, $(CH_2)_mNR^{14}R^{15}$, T"—$(CH_2)_mQ"R^{14}$, CO—T"—$(CH_2)_mQ"R^{14}$, $NH(CO)T"(CH_2)_mQ"R^{14}$, T"—$(CH_2)_mCO_2R^{14}$, or T"$(CH_2)_mCONR^{14}R^{15}$;
wherein T" and Q" are as defined above for T and Q;
$R^8$ is $C_1$–$C_6$ alkyl or $C_3$–$C_6$ cycloalkyl; and
Y is a halo counter-ion.
Preferred groups of compounds of Formula I are those wherein: (a) W is NH; (b) X is N; (c) Z is O; (d) $R^1$ is cycloalkyl, substituted cycloalkyl, alkyl, substituted alkyl, phenyl, substituted phenyl, pyridyl, or substituted pyridyl; (e) $R^2$ is alkyl, substituted alkyl, cycloalkyl, or substituted cycloalkyl; (f) $R^9$ is hydrogen or alkyl; and (g) $R^3$ is cycloalkyl, substituted cycloalkyl, alkyl, substituted alkyl, phenyl, substituted phenyl, pyridyl or substituted pyridyl; or more preferably, $R^3$ is hydrogen; or (h) combinations thereof.
Another preferred groups of compounds of Formula I are those wherein: (a) W is NH; (b) X is N; (c) Z is $NR^{10}$; (d) $R^2$ is hydrogen; (e) $R^1$ is cycloalkyl, substituted cycloalkyl, alkyl, substituted alkyl, phenyl, substituted phenyl, pyridyl, or substituted pyridyl; (f) $R^9$ is hydrogen or alkyl; and (g) $R^3$ is hydrogen, cycloalkyl, substituted cycloalkyl, alkyl, substituted alkyl, phenyl, substituted phenyl, pyridyl or substituted pyridyl; or (h) combinations thereof.
A further group of compounds of Formula I are those wherein: (a) W is NH; (b) X is CH; (c) Z is O or $NR^{10}$; (d) $R^1$ is cycloalkyl, substituted cycloalkyl, alkyl, substituted alkyl, phenyl, substituted phenyl, pyridyl, or substituted pyridyl; (e) $R^2$ is alkyl, substituted alkyl, cycloalkyl, or substituted cycloalkyl; or, alternatively, $R^2$ is hydrogen; (f) $R^9$ is hydrogen or alkyl; and (g) $R^3$ is hydrogen, cycloalkyl, substituted cycloalkyl, alkyl, substituted alkyl, phenyl, substituted phenyl, pyridyl or substituted pyridyl; or (h) combinations thereof.
Another group of compounds of Formula I are those wherein: (a) W is NH; (b) X is N; (c) Z is O or $NR^{10}$, and $R^3$ is H or substituted aryl or pyridyl; (d) $R^9$ is hydrogen; (e) Z is O, and $R^2$ is Me, Et, Pr, i-Pr, i-Bu, i-pentyl, or $C_3$–$C_7$ cycloalkyl; (f) X is CH; (g) $R^9$ is methyl; (h) $R^2$ is cycloalkyl and $R^9$ is heterocyclyl; (i) $R^3$ is $(CH_2)_n$Ar; or (j) combinations thereof. In an especially preferred group of compounds, Z is O and $R^2$ is cyclopentyl or ethyl.
In yet other preferred groups of compounds of Formula I: (h) Z is O, W is NH, and $R^1$ is alkyl, substituted alkyl, phenyl, substituted phenyl, pyridyl or substituted pyridyl; (i) Preferred $R^1$ substituted phenyl groups include 4-piperidinyl and 4-morpholino (with or without substitution), 4-(2-diethylaminoethoxy), 4-pyrrole, 4-pyrazol, and 4-(4-substituted piperazin-1-yl); (j) Z is O, and $R^1$ is phenyl substituted with hydroxy, alkoxy, $NR^5R^6$, or $T(CH_2)_mQR^4$. In more preferred compounds, Z is O, and $R^1$ is pyridyl substituted with $NR^5R^6$ or $T(CH_2)_mQR^4$; or Z is O, and $R^3$ is phenyl substituted with hydroxy, alkoxy, $NR^5R^6$, or $T(CH_2)_mQR^4$.
Compounds of Formula I wherein W is S, SO, or $SO_2$ are especially useful as intermediates leading to compounds where W is NH, but such compounds also display inhibitory activity against cyclin-dependent kinases and tyrosine kinases.
Unless otherwise expressly stated, the following definitions are adhered to throughout this disclosure.
"Alkyl" or "$C_1$–$C_{10}$ alkyl" means a straight or branched hydrocarbon radical having from 1 to 10 carbon atoms (unless stated otherwise) and includes, for example, methyl, ethyl, n-propyl, isopropyl, n-butyl, sec-butyl, isobutyl, tert-butyl, n-pentyl, isopentyl, n-hexyl, and the like. The term "$C_1$–$C_{10}$ alkyl" includes within its definition, for example, the terms "$C_1$–$C_3$ alkyl", "$C_1$–$C_4$ alkyl" and "$C_1$–$C_6$ alkyl".

"Halo" includes fluoro, chloro, bromo, and iodo.

"Alkenyl" or "$C_2$-$C_{10}$ alkenyl" means straight and branched hydrocarbon radicals having from 2 to 10 carbon atoms and one or two double bonds and includes ethenyl, 3-buten-1-yl, 2-ethenylbutyl, 3-hexen-1-yl, 3,6-octadien-1-yl, and the like. The term "$C_2$-$C_{10}$ alkenyl" includes within its definition, for example, the terms "$C_2$-$C_4$ alkenyl" and "$C_2$-$C_6$ alkenyl".

"Alkynyl" or "$C_2$-$C_{10}$ alkynyl" means straight and branched hydrocarbon radicals having from 2 to 10 carbon atoms and one or two triple bonds and includes ethynyl, 3-butyn-1-yl, propynyl, 2-butyn-1-yl, 3-pentyn-1-yl, 3,6-octadien-1-yl, and the like. The term "$C_2$-$C_{10}$ alkynyl" includes within its definition, for example, the terms "$C_2$-$C_4$ alkynyl" and "$C_2$-$C_6$ alkynyl".

"Cycloalkyl" or "$C_3$-$C_{10}$ cycloalkyl" means a monocyclic or polycyclic hydrocarbyl group such as cyclopropyl, cycloheptyl, cyclooctyl, cyclodecyl, cyclobutyl, adamantyl, norpinanyl, decalinyl, norbornyl, cyclohexyl, and cyclopentyl. Such groups can be substituted with groups such as hydroxy, keto, and the like. Also included are rings in which 1 to 3 heteroatoms replace carbons. Such groups are termed "heterocyclyl" or "$C_3$-$C_6$ heterocyclyl," which means a cycloalkyl group also bearing at least one heteroatom selected from O, S, or $NR_2$, examples being oxiranyl, pyrrolidinyl, piperidyl, tetrahydropyran, and morpholine. The term "$C_3$-$C_{10}$ cycloalkyl" includes within its definition, for example, the terms "$C_3$-$C_8$ cycloalkyl" and "$C_3$-$C_6$ cycloalkyl". The term "$C_3$-$C_6$ heterocyclyl" includes within its definition, for example, the "$C_3$-$C_5$ heterocyclyl".

"Alkoxy" or "$C_1$-$C_4$ alkoxy" refers to the alkyl groups mentioned above bound through oxygen, examples of which include methoxy, ethoxy, isopropoxy, tert-butoxy, and the like. In addition, alkoxy refers to polyethers such as —O—$(CH_2)_2$—O—$OH_3$, and the like.

"Alkanoyl" groups are alkyl linked through a carbonyl, i.e., $C_1$-$C_9$—C(O)—. Such groups include formyl, acetyl, propionyl, butyryl, and isobutyryl.

"Acyl" means an alkyl or aryl (Ar) group bonded through a carbonyl group, ie, R—C(O)—. For example, acyl includes a $C_1$-$C_{10}$ alkanoyl, including substituted alkanoyl, wherein the alkyl portion can be substituted by $NR^4R^5$ or a carboxylic or heterocyclic group. Typical acyl groups include acetyl, benzoyl, and the like.

The alkyl, cycloalkyl, alkenyl, alkoxy, and alkynyl groups described above are optionally substituted, preferably by 1 to 3 groups selected from $NR^5R^6$, $N(O)R^5R^6$, $NR^5R^6R^7Y$, $C_1$-$C_4$ alkyl, phenyl, substituted phenyl, thio $C_1$-$C_{10}$ alkyl, $C_1$-$C_{10}$ alkoxy, hydroxy, carboxy, $C_1$-$C_{10}$ alkoxycarbonyl, halo, nitrile, cycloalkyl, and a 5- or 6-membered carbocyclic ring or heterocyclic ring having 1 or 2 heteroatoms selected from nitrogen, substituted nitrogen, oxygen, and sulfur. "Substituted nitrogen" means nitrogen bearing $C_1$-$C_{10}$ alkyl or $(CH_2)_n$Ph where n is 0, 1, 2, or 3. "Substituted sulfur" means sulfur bearing $C_1$-$C_{10}$ alkyl or $(CH_2)_n$Ph where n is 0, 1, 2, or 3. Perhalo and polyhalo substitution is also embraced.

Examples of substituted alkyl groups include 2-aminoethyl, pentachloroethyl, trifluoromethyl, 2-diethylaminoethyl, 2-dimethylaminopropyl, ethoxycarbonylmethyl, 3-phenylbutyl, methanylsulfanylmethyl, methoxymethyl, 3-hydroxypentyl, 2-carboxybutyl, 4-chlorobutyl, 3-cyclopropylpropyl, pentafluoroethyl, 3-morpholinopropyl, piperazinylmethyl, and 2-(4-methylpiperazinyl)ethyl.

Examples of substituted alkynyl groups include 2-methoxyethynyl, 2-ethylsulfanyethynyl, 4-(1-piperazinyl)-3-(butynyl), 3-phenyl-5-hexynyl, 3-diethylamino-3-butynyl, 4-chloro-3-butynyl, 4-cyclobutyl-4-hexenyl, and the like.

Typical substituted alkoxy groups include 2-aminoethoxy, trifluoromethoxy, 2-diethylaminoethoxy, 2-ethoxycarbonylethoxy, 3-hydroxypropoxy, 6-carboxhexyloxy, and the like.

Further examples of substituted alkyl, alkenyl, and alkynyl groups include dimethylaminomethyl, carboxymethyl, 4-dimethylamino-3-buten-1-yl, 5-ethylmethylamino-3-pentyn-1-yl, 4-morpholinobutyl, 4-tetrahydropyrinidylbutyl, 3-imidazolidin-1-ylpropyl, 4-tetrahydrothiazol-3-yl-butyl, phenylmethyl, 3-chlorophenylmethyl, and the like.

The terms "Ar" and "aryl" refer to unsubstituted and substituted aromatic groups. "Heteroaryl" or "$C_3$-$C_9$ heteroaryl" groups have from 3 to 9 ring atoms, from 1 to 4 of which are independently selected from the group consisting of O, S, and N. Preferred heteroaryl groups have 1 or 2 heteroatoms in a 5- or 6-membered aromatic ring. Mono and bicyclic aromatic ring systems are included in the definition of aryl and heteroaryl. Typical aryl and heteroaryl groups include phenyl, 3-chlorophenyl, 2,6-dibromophenyl, 2-pyridyl, 3-methyl-2-pyridyl, 3-benzothienyl, 2,4,6-tribromophenyl, 4-ethyl-2-benzothienyl, 2-furanyl, 3,4-diethyl-2-furanyl, 1-naphthyl, 4,7-dichloro-2-naphthyl, pyrrole, pyrazole, imidazole, thiazole, and the like. An especially preferred heteroaryl group is pyridyl. The term "$C_3$-$C_9$ heteroaryl" includes within its definition, for example, the terms "$C_3$-$C_6$ heteroaryl" and "$C_3$-$C_5$ heteroaryl".

The terms "aryloxy" and "heteroaryloxy", such as phenoxy and $C_3$-$C_6$ heteroaryloxy, refer to the aryl and heteroaryl groups, respectively, mentioned above bound through oxygen.

Preferred Ar groups are phenyl and phenyl substituted by 1, 2, or 3 groups independently selected from the group consisting of alkyl, alkoxy, thio, thioalkyl, hydroxy, —$COOR^7$, amino of the formula —$NR^5R^6$, $CONR^5R^6$, and $T(CH_2)_mQR^4$ or $T(CH_2)_mCO_2R^4$ wherein m is 1 to 6, T is O, S, $NR^4$, $N(O)R^4$, $NR^5R^6Y$, or $CR^4R^5$, Q is O, S, $NR^5$, $N(O)R^5$, or $NR^5R^6Y$ wherein $R^4$, $R^5$ and $R^6$, are as described above, and $R^7$ is H, alkyl or substituted alkyl, for example, methyl, 2-aminoethyl, trichloroethyl, diphenylmethyl, and the like. The alkyl and alkoxy groups can be substituted as defined above. For example, typical groups are carboxyalkyl, alkoxycarbonylalkyl, hydroxyalkyl, hydroxyalkoxy, and alkoxyalkyl.

The invention compound will be named herein according to the following position assignments

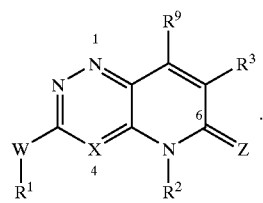

It will be appreciated by those skilled in the art that the compounds defined by the Formula I can exist in tautomeric forms. For example, a 6-keto compound can tautomerize to a 6-enol when $R^2$ is hydrogen as follows:

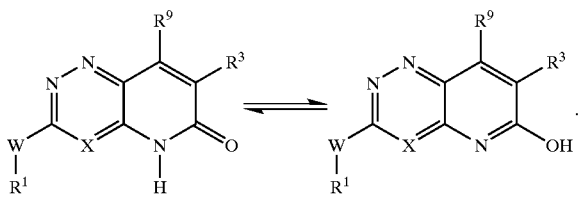

Similarly, 6-imino compounds can tautomerize to 6-amino compounds as follows:

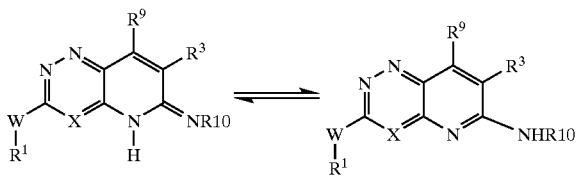

6-Thiones can tautomerize to thiols as follows:

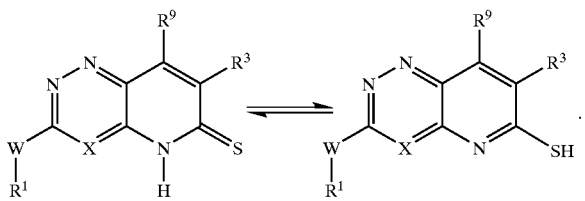

All of the tautomeric forms of the compounds are contemplated and included within the scope of this invention.

The compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of Formula I are capable of further forming both pharmaceutically acceptable formulations comprising salts, including but not limited to acid addition and/or base salts, solvates and N-oxides. This invention also provides pharmaceutical formulations and compositions comprising a compound of Formula I together with a pharmaceutically acceptable carrier, diluent, or excipient therefor. All of these forms are within the present invention.

Pharmaceutically acceptable acid addition salts of the compounds of Formula I include salts derived form inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge, et al., "Pharmaceutical Salts," *J. of Pharmaceutical Science*, 1977;66:1–19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention. Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge, et al., supra.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

The term "subject" means all animals, preferably mammals, including humans. Examples of subjects or mammals include humans, cows, dogs, cats, goats, sheep, and pigs.

The term "treating" for purposes of the present invention refers to prophylaxis or prevention, amelioration or elimination of a named disease or disorder once the disorder has been established.

The compounds of the present invention are useful for treating immunological disorders (for example, asthma, inflammatory disorders such as rheumatoid arthritis, autoimmune disorders such as autoimmune diabetes, and graft rejection associated with transplant surgery), cancer (for example, leukemia and cancer of the lung, breast, prostate, and skin such as melanoma) and other proliferative diseases including but not limited to angiogenesis, diabetic retinopathy, endometriosis, vascular smooth muscle cell proliferation, vascular smooth muscle cell proliferation associated with atherosclerosis, postsurgical vascular stenosis, psoriasis, surgical adhesions, macular degeneration, HSV, HIV, restenosis, and atherosclerosis. To utilize a compound of the present invention to treat cancer, a patient having cancer is administered a therapeutically effective amount of a disclosed compound or a pharmaceutically acceptable composition comprising the disclosed compound.

A further embodiment of this invention is a method of treating subjects suffering from diseases caused by vascular smooth muscle cell proliferation. Compounds within the scope of the present invention effectively inhibit vascular smooth muscle cell proliferation and migration. The method entails inhibiting vascular smooth muscle proliferation, and/or migration by administering an effective amount of a compound of Formula I to a subject in need of treatment.

The compounds of the present invention can be formulated and administered in a wide variety of oral and parenteral dosage forms, including transdermal and rectal administration. It will be recognized to those skilled in the art that the following dosage forms may comprise as the active component, a compound of Formula I or a corresponding pharmaceutically acceptable salt or solvate thereof.

A further embodiment of this invention is a pharmaceutical formulation comprising a compound of Formula I together with a pharmaceutically acceptable carrier, diluent, or excipient therefor. For preparing pharmaceutical compositions with the compounds of the present invention, pharmacuetically acceptable carriers can be either a solid or liquid. Solid form preparations include powders, tablets, pills, capsules, cachets, suppositories, and dispensible granules. A solid carrier can be one or more substances which may also act as diluents, flavoring agents, binders, preservatives, tablet disintegrating agents, or an encapsulating material.

In powders, the carrier is a finely divided solid such as talc or starch which is in a mixture with the finely divided active component. In tablets, the active component is mixed with the carrier having the necessary binding properties in suitable proportions and compacted in the shape and size desired.

The formulations of this invention preferably contain from about 5% to about 70% or more of the active compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. A preferred form for oral use are capsules, which include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogenously therein, as by stirring. The molten homogenous mixture is then poured into convenient size molds, allowed to cool, and thereby to solidify.

Liquid form preparations include solutions, suspensions, and emulsions such as water or water/propylene glycol solutions. For parenteral injection, liquid preparations can be formulated in solution in aqueous polyethylene glycol solution, isotonic saline, 5% aqueous glucose, and the like. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water and mixing with a viscous material, such as natural or synthetic gums, resins, methylcellulose, sodium carboxymethylcellulose, or other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. Waxes, polymers, microparticles, and the like can be utilized to prepare sustained-release dosage forms. Also, osmotic pumps can be employed to deliver the active compound uniformally over a prolonged period. The disclosed compounds can also be formulated as powders or liquids to be inhaled.

The pharmaceutical preparations of the invention are preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form.

The therapeutically effective dose or amount of a compound of Formula I will generally be from about 1 mg to about 100 mg/kg of body weight per day. Typical adult doses will be about 50 mg to about 800 mg per day. The quantity of active component in a unit dose preparation may be varied or adjusted from about 0.1 mg to about 500 mg, preferably about 0.5 mg to 100 mg according to the particular application and the potency of the active component. The composition can, if desired, also contain other compatible therapeutic agents. A subject in need of treatment with a compound of Formula I is administered a dosage of about 1 to about 500 mg per day, either singly or in multiple doses over a 24-hour period.

The compounds of the present invention are capable of binding to and inhibiting the activity of proteins having the ability to phosphorylate other proteins, such as cdks, PDGFr, FGFr, VEGF, c-Src, Lck and EGFr-FL. The compounds of this invention inhibit this phosphorylation and therefore can be used as anti-proliferative agents for the treatment of cancer and/or restenosis and other proliferative diseases.

Because of their inhibitory activity against cdks and other kinases, the compounds of the present invention are also useful research tools for studying the mechanism of action of those kinases, both in vitro and in vivo.

While the forms of the invention herein constitute presently preferred embodiments, many others are possible. It is not intended herein to mention all of the possible equivalent forms or ramifications of the invention. It is understood that the terms used herein are merely descriptive rather than limiting, and those skilled in the art will realize that various changes may be made without departing from the spirit or scope of the invention.

The following compounds illustrate specific embodiments provided by the present invention, and the compounds listed below are among the preferred embodiments:

5-Cyclopentyl-3-(pyridin-4-ylamino)-5H-pyrido[2,3-e]-1,2,4-triazin-6-one;

5-Cyclopentyl-8-methyl-3-(pyridin-4-ylamino)-5H-pyrido[2,3-e]-1,2,4-triazin-6-one;

4-(5-Cyclopentyl-6-oxo-5,6-dihydro-pyrido[2,3-e]-1,2,4-triazin-3-ylamino)-benzenesulfonamide;

4-(5-Cyclopentyl-8-methyl-6-oxo-5,6-dihydro-pyrido[2,3-e]-1,2,4-triazin-3-ylamino)-benzenesulfonamide;

5-Cyclopentyl-3-(4-piperazin-1-yl-phenylamino)-5H-pyrido[2,3-e]-1,2,4-triazin-6-one;

4-[4-(5-Cyclopentyl-6-oxo-5,6-dihydro-pyrido[2,3-e]-1,2,4-triazin-3-ylamino)-phenyl]-piperazine-1-carboxylic acid amide;

5-Cyclopentyl-8-methyl-3-(4-piperazin-1-yl-phenylamino)-5H-pyrido[2,3-e]-1,2,4-triazin-6-one;

4-[4-(5-Cyclopentyl-8-methyl-6-oxo-5,6-dihydro-pyrido[2,3-e]-1,2,4-triazin-3-ylamino)-phenyl]-piperazine-1-carboxylic acid amide;

5-Cyclopentyl-3-[4-(3,5-dimethyl-piperazin-1-yl)-phenylamino]-5H-pyrido[2,3-e]-1,2,4-triazin-6-one;

4-[4-(5-Cyclopentyl-6-oxo-5,6-dihydro-pyrido[2,3-e]-1,2,4-triazin-3-ylamino)-phenyl]-2,6-dimethyl-piperazine-1-carboxylic acid amide;

5-Cyclopentyl-3-[4-(3,5-dimethyl-piperazin-1-yl)-phenylamino]-8-methyl-5H-pyrido[2,3-e]-1,2,4-triazin-6-one;

4-[4-(5-Cyclopentyl-8-methyl-6-oxo-5,6-dihydro-pyrido[2,3-e]-1,2,4-triazin-3-ylamino)-phenyl]-2,6-dimethyl-piperazine-1-carboxylic acid amide;

7-(2-Chloro-3,5-dimethoxy-phenyl)-5-ethyl-3-(pyridin-4-ylamino)-5H-pyrido[2,3-e]-1,2,4-triazin-6-one;

7-(2,6-Dichloro-3,5-dimethoxy-phenyl)-5-ethyl-3-(pyridin-4-ylamino)-5H-pyrido[2,3-e]-1,2,4-triazin-6-one;

7-(3,5-Dimethoxy-2-methyl-phenyl)-5-ethyl-3-(pyridin-4-ylamino)-5H-pyrido[2,3-e]-1,2,4-triazin-6-one;

7-(3,5-Dimethoxy-phenyl)-5-ethyl-3-(pyridin-4-ylamino)-5H-pyrido[2,3-e]-1,2,4-triazin-6-one;

7-(3,5-Dimethoxy-2,6-dimethyl-phenyl)-5-ethyl-3-(pyridin-4-ylamino)-5H-pyrido[2,3-e]-1,2,4-triazin-6-one;

5-Cyclopentyl-7-(3,5-dimethoxy-phenyl)-3-(pyridin-4-ylamino)-5H-pyrido[2,3-e]-1,2,4-triazin-6-one;

7-(2-Chloro-3,5-dimethoxy-phenyl)-5-cyclopentyl-3-(pyridin-4-ylamino)-5H-pyrido[2,3-e]-1,2,4-triazin-6-one;

5-Cyclopentyl-7-(2,6-dichloro-3,5-dimethoxy-phenyl)-3-(pyridin-4-ylamino)-5H-pyrido[2,3-e]-1,2,4-triazin-6-one;

5-Cyclopentyl-7-(3,5-dimethoxy-2-methyl-phenyl)-3-(pyridin-4-ylamino)-5H-pyrido[2,3-e]-1,2,4-triazin-6-one;

5-Cyclopentyl-7-(3,5-dimethoxy-2,6-dimethyl-phenyl)-3-(pyridin-4-ylamino)-5H-pyrido[2,3-e]-1,2,4-triazin-6-one;

7-(2,6-Dimethoxy-pyridin-4-yl)-5-ethyl-3-(pyridin-4-ylamino)-5H-pyrido[2,3-e]-1,2,4-triazin-6-one;

7-(3-Chloro-2,6-dimethoxy-pyridin-4-yl)-5-ethyl-3-(pyridin-4-ylamino)-5H-pyrido [2,3-e]-1,2,4-triazin-6-one;

7-(3,5-Dichloro-2,6-dimethoxy-pyridin-4-yl)-5-ethyl-3-(pyridin-4-ylamino)-5H-pyrido[2,3-e]-1,2,4-triazin-6-one;

5-Cyclopentyl-7-(2,6-dimethoxy-pyridin-4-yl)-3-(pyridin-4-ylamino)-5H-pyrido[2,3-e]-1,2,4-triazin-6-one;

7-(3-Chloro-2,6-dimethoxy-pyridin-4-yl)-5-cyclopentyl-3-(pyridin-4-ylamino)-5H-pyrido[2,3-e]-1,2,4-triazin-6-one;

5-Cyclopentyl-7-(3,5-dichloro-2,6-dimethoxy-pyridin-4-yl)-3-(pyridin-4-ylamino)-5H-pyrido[2,3-e]-1,2,4-triazin-6-one;

7-(2-Chloro-3,5-dimethoxy-phenyl)-3-[4-(2-diethylamino-ethoxy)-phenylamino]-5-ethyl-5H-pyrido[2,3-e]-1,2,4-triazin-6-one;

7-(2,6-Dichloro-3,5-dimethoxy-phenyl)-3-[4-(2-diethylamino-ethoxy)-phenylamino]-5-ethyl-5H-pyrido[2,3-e]-1,2,4-triazin-6-one;

3-[4-(2-Diethylamino-ethoxy)-phenylamino]-7-(3,5-dimethoxy-2-methyl-phenyl)-5-ethyl-5H-pyrido[2,3-e]-1,2,4-triazin-6-one;

3-(4-Diethylamino-butylamino)-7-((3,5-dimethoxy-phenyl)-5-ethyl-5H-pyrido[2,3-e]-1,2,4-triazin-6-one;

3-[4-(2-Diethylamino-ethoxy)-phenylamino]-7-(3,5-dimethoxy-2,6-dimethyl-phenyl)-5-ethyl-5H-pyrido[2,3-e]-1,2,4-triazin-6-one;

5-Cyclopentyl-3-[4-(2-diethylamino-ethoxy)-phenylamino]-7-(3,5-dimethoxy-phenyl)-5H-pyrido[2,3-e]-1,2,4-triazin-6-one;

7-(2-Chloro-3,5-dimethoxy-phenyl)-5-cyclopentyl-3-[4-(2-diethylamino-ethoxy)-phenylamino]-5H-pyrido[2,3-e]-1,2,4-triazin-6-one;

5-Cyclopentyl-7-(2,6-dichloro-3,5-dimethoxy-phenyl)-3-[4-(2-diethylamino-ethoxy)-phenylamino]-5H-pyrido[2,3-e]-1,2,4-triazin-6-one;

5-Cyclopentyl-3-[4-(2-diethylamino-ethoxy)-phenylamino]-7-(3,5-dimethoxy-2-methyl-phenyl)-5H-pyrido[2,3-e]-1,2,4-triazin-6-one;

5-Cyclopentyl-3-[4-(2-diethylamino-ethoxy)-phenylamino]-7-(3,5-dimethoxy-2,6-dimethyl-phenyl)-5H-pyrido[2,3-e]-1,2,4-triazin-6-one;

3-[4-(2-Diethylamino-ethoxy)-phenylamino]-7-(2,6-dimethoxy-pyridin-4-yl)-5-ethyl-5H-pyrido[2,3-e]-1,2,4-triazin-6-one;

7-(3-Chloro-2,6-dimethoxy-pyridin-4-yl)-3-[4-(2-diethylamino-ethoxy)-phenylamino]-5-ethyl-5H-pyrido[2,3-e]-1,2,4-triazin-6-one;

7-(3,5-Dichloro-2,6-dimethoxy-pyridin-4-yl)-3-[4-(2-diethylamino-ethoxy)-phenylamino]-5-ethyl-5H-pyrido[2,3-e]-1,2,4-triazin-6-one;

7-(2-Chloro-3,5-dimethoxy-phenyl)-3-(4-diethylamino-butylamino)-5-ethyl-5H-pyrido[2,3-e]-1,2,4-triazin-6-one;

7-(2,6-Dichloro-3,5-dimethoxy-phenyl)-3-(4-diethylamino-butylamino)-5-ethyl-5H-pyrido[2,3-e]-1,2,4-triazin-6-one;

3-(4-Diethylamino-butylamino)-7-(3,5-dimethoxy-2-methyl-phenyl)-5-ethyl-5H-pyrido[2,3-e]-1,2,4-triazin-6-one;

3-(4-Diethylamino-butylamino)-7-(3,5-dimethoxy-2,6-dimethyl-phenyl)-5-ethyl-5H-pyrido[2,3-e]-1,2,4-triazin-6-one;

5-Cyclopentyl-3-(4-diethylamino-butylamino)-7-(3,5-dimethoxy-phenyl)-5H-pyrido[2,3-e]-1,2,4-triazin-6-one;

7-(2-Chloro-3,5-dimethoxy-phenyl)-5-cyclopentyl-3-(4-diethylamino-butylamino)-5H-pyrido[2,3-e]-1,2,4-triazin-6-one;

5-Cyclopentyl-7-(2,6-dichloro-3,5-dimethoxy-phenyl)-3-(4-diethylamino-butylamino)-5H-pyrido[2,3-e]-1,2,4-triazin-6-one;

5-Cyclopentyl-3-(4-diethylamino-butylamino)-7-(3,5-dimethoxy-2-methyl-phenyl)-5H-pyrido[2,3-e]-1,2,4-triazin-6-one;

5-Cyclopentyl-3-(4-diethylamino-butylamino)-7-(3,5-dimethoxy-2,6-dimethyl-phenyl)-5H-pyrido[2,3-e]-1,2,4-triazin-6-one;

3-(4-Diethylamino-butylamino)-7-(2,6-dimethoxy-pyridin-4-yl)-5-ethyl-5H-pyrido[2,3-e]-1,2,4-triazin-6-one;

7-(3-Chloro-2,6-dimethoxy-pyridin-4-yl)-3-(4-diethylamino-butylamino)-5-ethyl-5H-pyrido[2,3-e]-1,2,4-triazin-6-one;

7-(3,5-Dichloro-2,6-dimethoxy-pyridin-4-yl)-3-(4-diethylamino-butylamino)-5-ethyl-5H-pyrido[2,3-e]-1,2,4-triazin-6-one;

5-Cyclopentyl-3-(4-diethylamino-butylamino)-7-(2,6-dimethoxy-pyridin-4-yl)-5H-pyrido[2,3-e]-1,2,4-triazin-6-one;

7-(3-Chloro-2,6-dimethoxy-pyridin-4-yl)-5-cyclopentyl-3-(4-diethylamino-butylamino)-5H-pyrido[2,3-e]-1,2,4-triazin-6-one;

5-Cyclopentyl-7-(3,5-dichloro-2,6-dimethoxy-pyridin-4-yl)-3-(4-diethylamino-butylamino)-5H-pyrido[2,3-e]-1,2,4-triazin-6-one;

7-Acetyl-5-cyclopentyl-8-methyl-3-(4-piperazin-1-yl-phenylamino)-5H-pyrido[2,3-e][1,2,4]triazin-6-one;

5-Cyclopentyl-8-methyl-6-oxo-3-(4-piperazin-1-yl-phenylamino)-5,6-dihydro-pyrido[2,3-e][1,2,4]triazine-7-carboxylic acid ethyl ester;

7-Acetyl-5-cyclopentyl-3-(4-piperazin-1-yl-phenylamino)-5H-pyrido[2,3-e][1,2,4]triazin-6-one;

7-Benzyl-5-cyclopentyl-3-(4-piperazin-1-yl-phenylamino)-5H-pyrido[2,3-e][1,2,4]triazin-6-one;

7-Benzyl-5-cyclopentyl-3-(4-piperazin-1-yl-cyclohexylamino)-5H-pyrido[2,3-e][1,2,4]triazin-6-one;
7-Benzyl-5-cyclopentyl-3-(4-dimethylamino-cyclohexylamino)-5H-pyrido[2,3-e][1,2,4]triazin-6-one;
7-Bromo-5-cyclopentyl-3-(4-piperazin-1-yl-phenylamino)-5H-pyrido[2,3-e][1,2,4]triazin-6-one;
7-Bromo-5-cyclopentyl-8-methyl-3-(4-piperazin-1-yl-phenylamino)-5H-pyrido[2,3-e][1,2,4]triazin-6-one;
7-Benzyl-5-cyclopentyl-3-(1-propyl-piperidin-4-ylamino)-5H-pyrido[2,3-e][1,2,4]triazin-6-one;
7-Benzyloxy-5-cyclopentyl-3-(4-piperazin-1-yl-phenylamino)-5H-pyrido[2,3-e][1,2,4]triazin-6-one;
5-Cyclopentyl-7-ethyl-3-(4-piperazin-1-yl-phenylamino)-5H-pyrido[2,3-e][1,2,4]triazin-6-one;
5-Cyclopentyl-3-(4-piperazin-1-yl-phenylamino)-7-propoxy-5H-pyrido[2,3-e][1,2,4]triazin-6-one;
5-Cyclopentyl-3-(4-piperazin-1-yl-phenylamino)-7-o-tolylamino-5H-pyrido[2,3-e][1,2,4]triazin-6-one;
5-Cyclopentyl-7-(4-methoxy-phenylamino)-3-(4-piperazin-1-yl-phenylamino)-5H-pyrido[2,3-e][1,2,4]triazin-6-one; and
5-Cyclopentyl-7-(2-ethoxy-ethoxy)-3-(4-piperazin-1-yl-phenylamino)-5H-pyrido[2,3-e][1,2,4]triazin-6-one.
7-(3,5-Dimethoxy-phenyl)-5-ethyl-3-(pyridin-4-ylamino)-5H-pyrido[2,3-e]-1,2,4-triazin-6-one.
3-(4-Diethylamino-butylamino)-7-(3,5-dimethoxy-phenyl)-5-ethyl-5H-pyrido[2,3-e]-1,2,4-triazin-6-one.

Compounds of Formula I wherein X is N or CH may be prepared according to the syntheses outlined in Schemes 1–3. Although these schemes often indicate exact structures, those with ordinary skill in the art will appreciate that the methods apply widely to analogous compounds of Formula I, given appropriate consideration to protection and deprotection of reactive functional groups by methods standard to the art of organic chemistry. For example, hydroxy groups, in order to prevent unwanted side reactions, generally need to be converted to ethers or esters during chemical reactions at other sites in the molecule. The hydroxy protecting group is readily removed to provide the free hydroxy group. Amino groups and carboxylic acid groups are similarly derivatized to protect them against unwanted side reactions. Typical protecting groups and methods for attaching and cleaving them are described fully by Greene and Wuts in *Protective Groups in Organic Synthesis*, John Wiley and Sons, New York, (2nd Ed., 1991), and McOmie, *Protective Groups in Organic Chemistry*, Plenum Press, New York, 1973.

Scheme 1 describes a typical method for the preparation of the compounds of the invention illustrated by Formula II

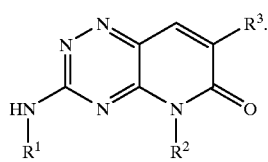

II

The synthesis begins with the acid catalyzed coupling of diethyl ketomalonate and thiosemicarbazide in ethanol. To the cooled reaction is added sodium metal to complete the cyclization to provide 5-hydroxy-3-mercapto-1,2,4-triazine-6-carboxylic acid ethyl ester. Alkylation of the sulfur with an alkylating agent such as methyl iodide and a common base such as potassium carbonate in a solvent like dimethylformamide affords 5-hydroxy-3-methylsulfanyl-1,2,4-triazine-6-carboxylic acid ethyl ester. Transformation of the hydroxy group to chloro with thionylchloride gives a key intermediate to which amino groups can be added to provide 5-alkylamino-3-methylsulfanyl-1,2,4-triazine-6-carboxylic acid, ethyl ester. The amine used can be anhydrous or in an aqueous solution, as with methyl or ethyl amine, or cyclopentylamine. The use of aqueous ammonium hydroxide provides the corresponding primary amine at C-5 position. Conversion of the ester group to an aldehyde can be accomplished by reduction to the alcohol with a reducing agent such as lithium aluminum hydride in a solvent like tetrahydrofuran followed by mild oxidation with manganese dioxide to provide 5-alkylamino-3-methylsulfanyl-1,2,4-triazine-6-carbaldehyde. Cyclization is accomplished by the reaction of the above triazine with an agent such as substituted phenyl acetonitrile and a base such as potassium carbonate in a solvent like tetrahydrofuran. Hydrolysis of the resulting C-6 imine under mild acidic reaction conditions gives 7-substituted phenyl-5-alkyl-3-methylsulfanyl-pyrido-1,2,4-triazin-6-one. Ultimately, the 7-substituted phenyl-5-alkyl-3-amino-pyrido-1,2,4-triazin-6-one is obtained by the reaction of the methylthio compound with an amine with or without a solvent. The temperature and conditions required for the displacement depends upon the amine used. Aromatic, secondary, and tertiary amines usually require higher temperatures than primary aliphatic or benzyl amines. When aromatic amines such as aniline or aminopyridine are used, the reaction is usually run with the amine as the solvent at high temperatures (e.g., 80–150° C.).

Scheme 2 describes how another set of preferred compounds of this invention, illustrated by Formula III

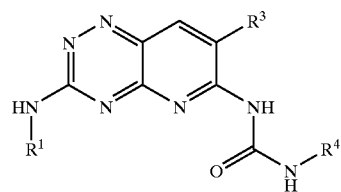

III can be prepared if ammonia is used to displace the chloro group of 5-chloro-3-methylsulfanyl-1,2,4-triazine-6-carboxylic acid, ethyl ester to give 5-amino-3-methylsulfanyl-1,2,4-triazine-6-carboxylic acid, ethyl ester. The aldehyde is obtained and reacted with a substituted phenyl acetonitrile as described above to provide the 6-amino-pyridotriazines. The methylthio group is displaced as described above, also, and the 6-amino group of the resulting 6-amino-7-substituted phenyl-3-substituted amino-pyrido-1,2,4-triazine is derivatized by standard methods, for example alkylation or acylation, to provide compounds of Formula III.

Scheme 3 describes a typical method for the preparation of yet another set of compounds of this invention, illustrated by Formula IV

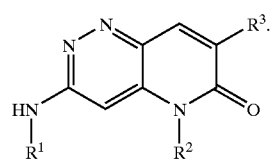

IV

The synthesis begins with the coupling of hydrazine and the dialkyl ester of chloromaleic acid followed by the conversion of the resulting carbonyl groups to chloro groups with phosphorous oxychloride to give the 3,4,6-trichloropyridazine. Displacement of the chloro group at C-4 with a primary amine like ethylamine or cyclopentylamine in a solvent like diethyl ether or dichloromethane at cool reaction temperature (for example below 0° C.) followed by the displacement of the chloro group at C-6 with another appropriate primary amine like aniline or 4-aminopyridine provides the intermediate whereby the C-4 and C-6 positions of the pyridazine are appropriately substituted with amino groups. Halogen exchange of the remaining chloro group at C-3 to iodo in a heated reaction with KI in DMSO or by the reaction of butyllithium and iodine gives the 3-iodo intermediate that is transformed to the carboxaldehyde via a palladium catalyzed carbonylation utilizing carbon monoxide and tributyltin hydride. The resulting 4,6-diaminopyridazine-3-carboxaldehyde is then converted to compounds of Formula IV where $R^3$ is H via Horner-Emmons reaction conditions or where R is a substituent like an aryl group via Aldol reaction conditions such as potassium carbonate in dimethylformamide or sodium hydride in tetrahydrofuran.

Pyrido[2,3-e][1,2,4]triazinin-6-ones are available through the route illustrated in Scheme 4. The intermediate aldehyde from Scheme 1 may be converted under Homer Emmons or aldol conditions to the pyridotriazinone with various substituents $R_3$. Straight displacement of the sulfide with strong nucleophiles such as primary amines or initial conversion of the sulfide to the chloride followed by displacement of Cl will produce the final product. Compounds with substituents at $R^9$ are similarly available after first converting the aldehyde to a ketone via a Grignard reaction/oxidation sequence. Halogenated products may be further converted to ethers, esters, ketones and amines as shown in Schemes 5–8.

Scheme 1

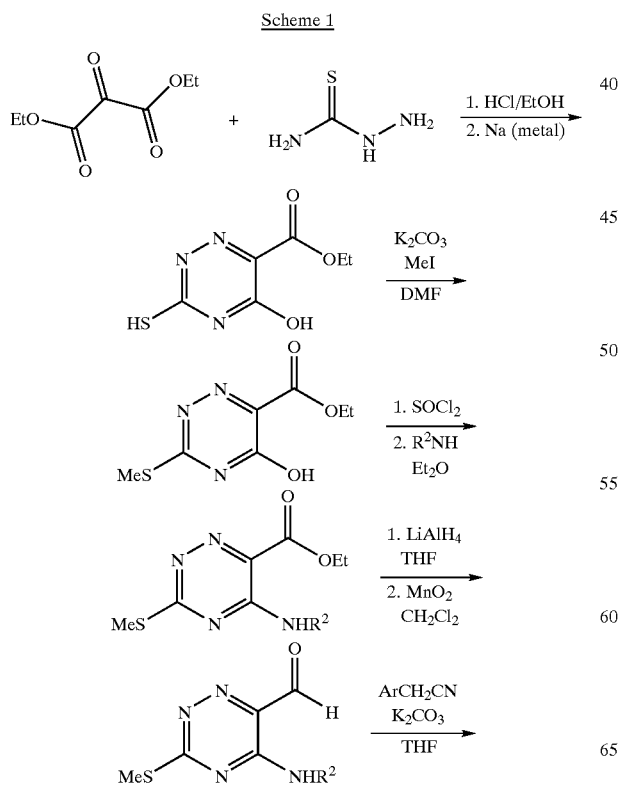

Scheme 2

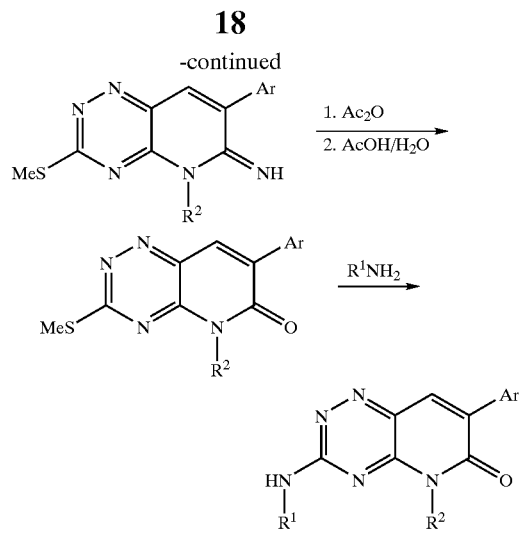

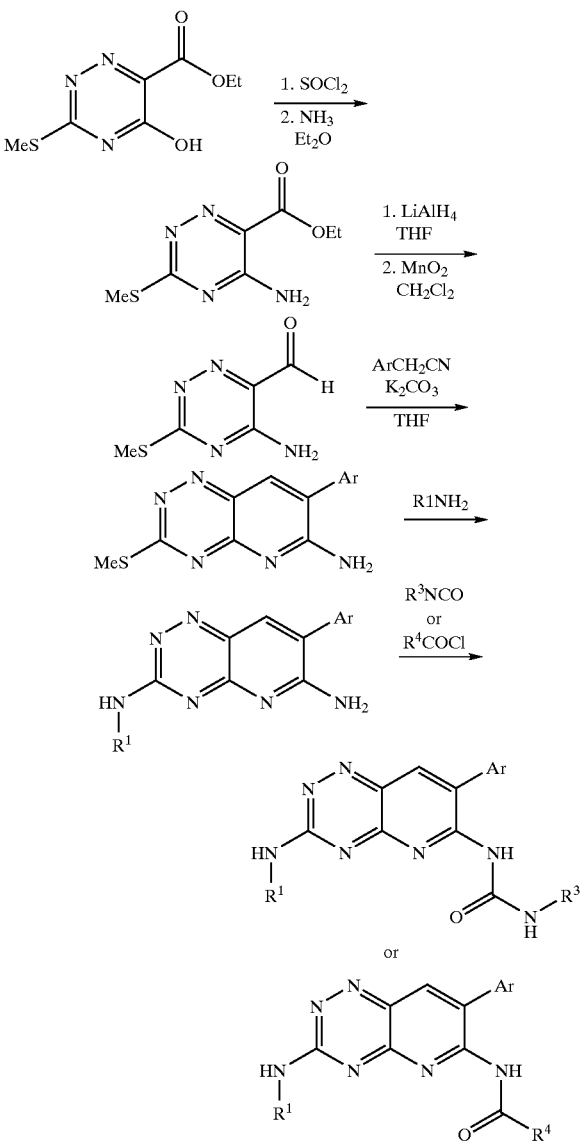

Scheme 3
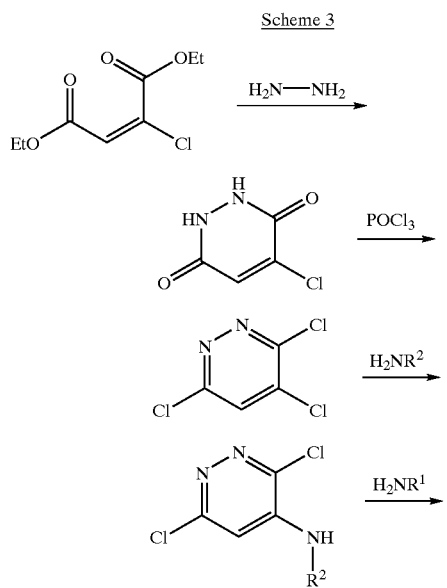
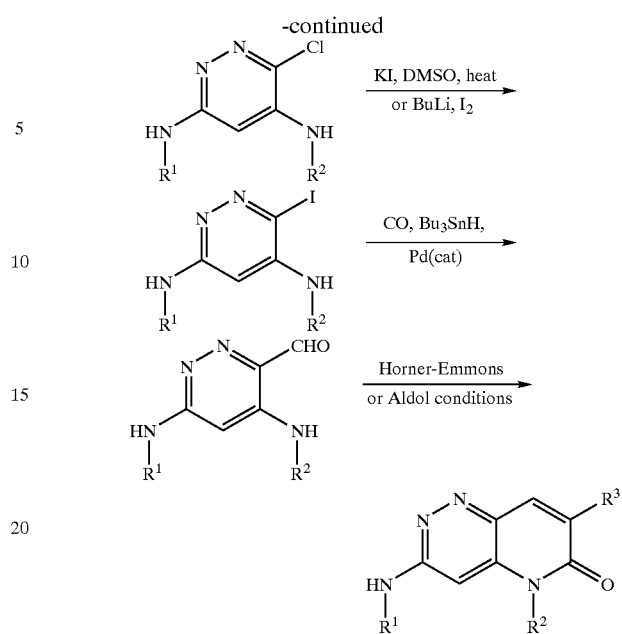
Scheme 4
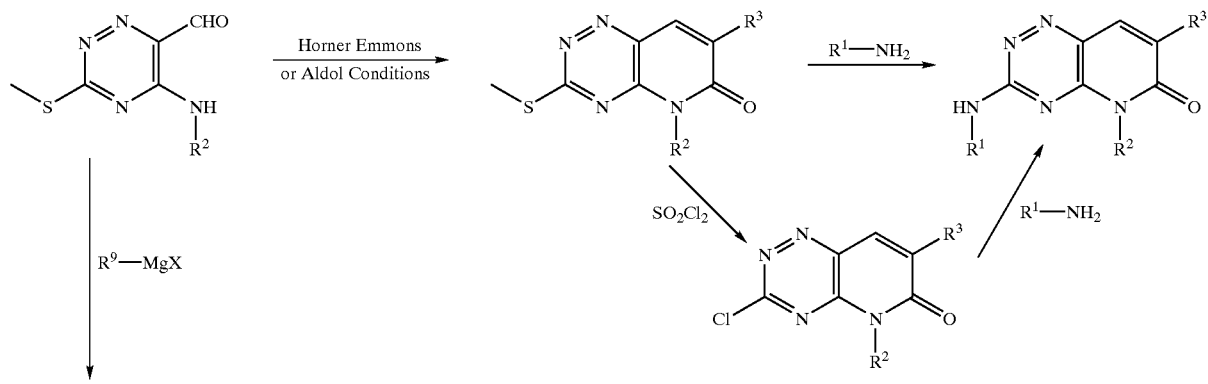
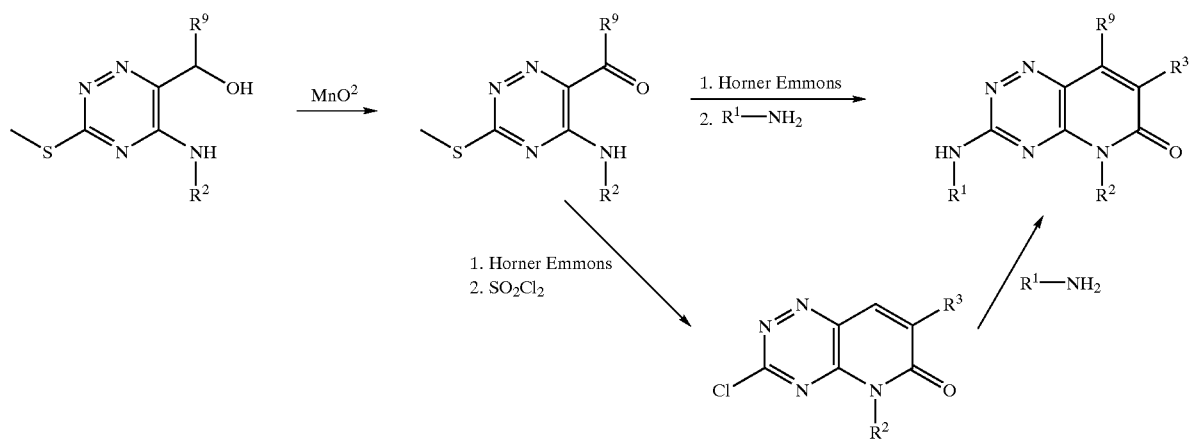

Scheme 5

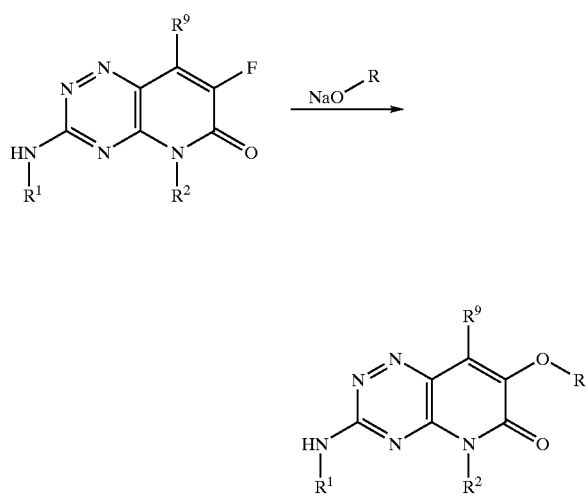

Scheme 6

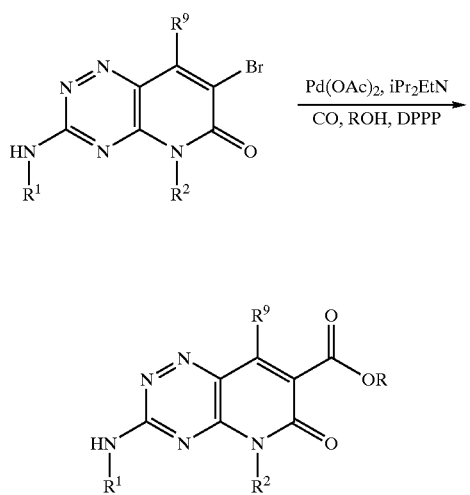

Scheme 7

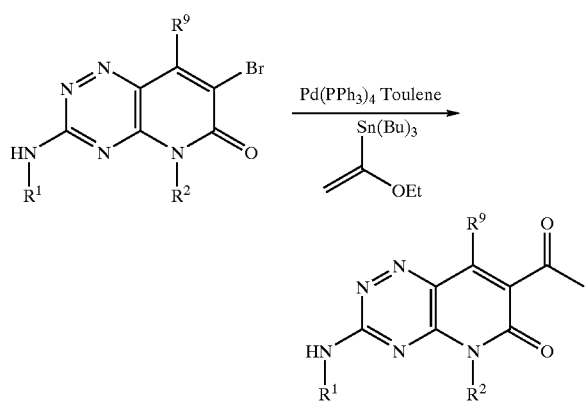

Scheme 8

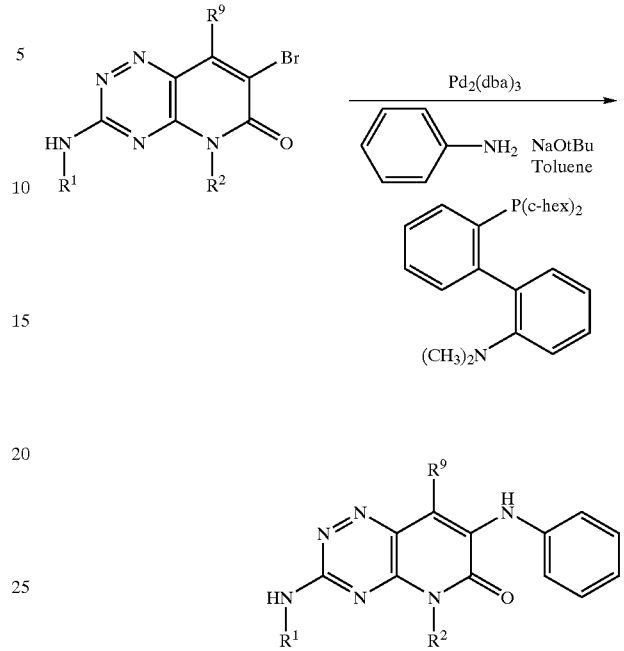

All of the disclosed compounds are readily purified by standard methods when desired. Typical purification steps employed include chromatography over solid supports such as silica gel or alumina. Elution generally is carried out using common solvents such as acetone, ethyl acetate, tetrahydrofuran, ethanol, triethylamine, and mixtures of such solvents. Other purification processes can similarly be employed, including crystallization from common solvents such as methanol, ethanol, diethyl ether, ethyl acetate, and the like. Sometimes such crystallizations can afford solvates such as an ethanol solvate, as well as hydrates, and all such solvates and hydrates are included in the scope of this invention.

The foregoing general reaction schemes are further described by the following detailed examples which are for illustrative purposes only and are not intended, nor should they be construed, as limiting the invention in any manner. Those skilled in the art will appreciate that variations and modifications can be made without violating the spirit or scope of the invention.

EXAMPLE 1

5-Hydroxy-3-mercapto-1,2,4-triazine-6-carboxylic acid, ethyl ester

To a room temperature solution of 50.0 g (287.1 mmol, 43.8 mL) of diethylketomalonate in 1.1 L of ethanol was added 26.2 g (287.1 mmol) of thiosemicarbazide. To this reaction mixture was added 10.3 mL (124 mmol) of concentrated HCl. The reaction mixture was heated at 50° C. to 55° C. for 2 hours, then cooled to 5° C.

To the above reaction mixture was carefully added 9.45 g (410.5 mmol) of sodium metal while keeping the reaction temperature below 40° C. The reaction was complete when all the sodium had dissolved. The reaction mixture was concentrated to near dryness, diluted with 600 mL of ethyl acetate, and washed with 205 mL of 2N HCl, then with water, and brine. The organic phase was dried over magnesium sulfate and filtered. The aqueous phase was saturated with solid sodium chloride and extracted twice with ethyl acetate. This latter organic phase was dried over magnesium sulfate, filtered, combined with the former, concentrated, and dried under house vacuum to give 52.8 g (91%) of a yellow solid. Mp=202–205° C. (dec).

EXAMPLE 2

5-Hydroxy-3-methylsulfanyl-1,2,4-triazine-6-carboxylic acid ethyl ester

To a 0° C. solution of 29.0 g (144.1 mmol) of 5-hydroxy-3-mercapto-1,2,4-triazine-6-carboxylic acid ethyl ester in 75 mL of DMF was added 14.4 g (144.1 mmol) of potassium carbonate. The reaction mixture was stirred for 1 hour, and 24.2 mL (389.2 mmol) of methyl iodide was added as fast as the effervescence would allow. The ice bath was removed, and the reaction was covered with a nitrogen filled balloon and stirred at room temperature overnight.

The reaction mixture was concentrated under vacuum. Saturated sodium bicarbonate was added until there was no more effervescence, approximately 225 mL. This aqueous phase was washed 2 times with ethyl acetate, was cooled in an ice bath, and concentrated HCl was added to adjust the pH to 3–5. This aqueous phase was extracted 4 times with dichloromethane. The combined dichloromethane was washed with water, then brine, dried over magnesium sulfate, filtered, and concentrated. The last traces of solvents including DMF were removed under high vacuum to give 29.2 g of yellow-orange solid. The residue was triturated under 50 mL of 2:3 ethyl acetate/hexane for several hours, filtered to give 13.9 g (45%) of off-white solid. Mp=139–141° C.

NMR: consistent with that reported in J. Huang, JOC 1985;50:2294.

MS (APCI) (m+1)/z 216.

Analysis calculated for $C_7H_9N_3O_3S$: C, 39.06; H, 4.21; N, 19.52.

Found: C, 38.95; H, 4.07; N, 19.40.

EXAMPLE 3

5-Ethylamino-3-methylsulfanyl-1,2,4-triazine-6-carboxylic acid, ethyl ester

To 17.0 g (78.98 mmol) of 5-hydroxy-3-methylsulfanyl-1,2,4-triazine-6-carboxylic acid, ethyl ester was added 86 mL (1184.7 mmol) of thionyl chloride. The reaction mixture was heated to 75° C. for 2 hours, cooled, and concentrated. The residue was twice suspended in toluene and concentrated to give a yellow-orange solid, 5-chloro-3-methylsulfanyl-1,2,4-triazine-6-carboxylic acid, ethyl ester.

Below the surface of a solution of the above crude product in 400 mL of diethyl ether was introduced gaseous ethylamine for 15 minutes. After completion of the reaction, based on silica tlc: 1:9 ethyl acetate/dichloromethane, the reaction mixture was filtered, and the solids were washed with diethyl ether. The filtrate was concentrated to a dark oil that solidified on standing. The solid was chromatographed on 700 g of silica eluted with 2:2:6 ethyl acetate/dichloromethane/hexane to give 16.2 g (85%) of yellow solid.

A portion of the crude product that was crystallized from ethanol/water gave the following characterization. MS (APCI) (m+1)/z 243.

Analysis calculated for $C_9H_{14}N_4O_2S$: C, 44.61; H, 5.82; N, 23.12.

Found: C, 44.78; H, 5.82; N, 22.96.

EXAMPLE 4

5-Ethylamino-3-methylsulfanyl-1,2,4-triazine-6-carbaldehyde

To a room temperature suspension of 5.1 g (133.7 mmol) of lithium aluminum hydride in 400 mL of anhydrous THF was added a solution of 16.2 g (66.9 mmol) of 5-ethylamino-3-methylsulfanyl-1,2,4-triazine-6-carboxylic acid, ethyl ester in 150 mL of THF. The reaction was stirred for 6 hours at room temperature, at which time approximately 16 mL of a saturated solution of ammonium sulfate was added dropwise while keeping the reaction temperature below 25° C. with an ice bath. The reaction mixture becomes heavy with precipitate, and 200 mL of THF was added followed by 5 mL more of saturated ammonium sulfate. The reaction mixture was stirred for another 30 minutes and decanted. The remaining solids were filtered and washed several times with a total of 1 L of hot THF. The combined THF solution was concentrated and twice dissolved in dichloromethane and concentrated to give a pale orange semi-solid, (5-ethylamino-3-methylsulfanyl-1,2,4-triazin-6-yl)-methanol.

To a solution of the crude product above in 640 mL of dichloromethane was added 96 g (1.1 mol) of manganese dioxide and the reaction mixture was stirred at room temperature overnight. The reaction mixture was filtered through a pad of celite which was washed well with dichloromethane and ethyl acetate. The combined organic solution was concentrated, and the dark residue was chromatographed on 500 g of silica eluted with 1:1 ethyl acetate/dichloromethane then ethyl acetate to give 5.9 g (44%) of the title compound. MS (APCI) (m+1)/z 199.1.

EXAMPLE 5

7-(3,5-Dimethoxy-phenyl)-5-ethyl-3-methylsulfanyl-5H-pyrido[2,3-e]-1,2,4-triazin-6-ylideneamine To a solution of 5.0 g (25.2 mmol) of 5-ethylamino-3-methylsulfanyl-1,2,4-triazine-6-carbaldehyde in 125 mL of THF was added 6.7 g (37.8 mmol) of 3,5-dimethoxyphenylacetonitrile followed by 17.4 g (126.1 mmol) of potassium carbonate. The reaction mixture was warmed at 65° C. for 2 days, concentrated under vacuum, diluted with ethyl acetate, and washed three times with a saturated solution of sodium bicarbonate, once with water and brine. The organic phase was dried over magnesium sulfate, filtered, decolorized with charcoal, filtered through celite, and concentrated to give a dark orange oil. The crude oil was chromatographed through silica eluted with 2:2:6 to 2:3:5 dichloromethane/ethyl acetate/hexane to give 5.4 g (59%) of the title compound as a yellow amorphous solid. MS (APCI) (m+1)/z 358.1.

Analysis calculated for $C_{17}H_{19}N_5O_2S$: C, 57.13; H, 5.36; N, 19.59.

Found: C, 57.10; H, 5.32; N, 19.39.

EXAMPLE 6

7-(3,5-Dimethoxy-phenyl)-5-ethyl-3-methylsulfanyl-5H-pyrido[2,3-e]-1,2,4-triazin-6-one To 4.7 g (13.2 mmol) of 7-(3,5-dimethoxy-phenyl)-5-ethyl-3-methylsulfanyl-5H-pyrido[2,3-e]-1,2,4-triazin-6- ylideneamine was added 55 mL of acetic anhydride. The reaction mixture was warmed at 90° C. overnight, and the very dark red solution was concentrated under house vacuum at 40° C. to give a dark brown residue, N-[7-(3,5-dimethoxy-phenyl)-5-ethyl-3-methylsulfanyl-5H-pyrido[2,3-e]-1,2,4-triazin-6-ylidene]-acetamide. MS (APCI) (m+1)/z 400.1.

To the dark brown residue was added 60 mL of acetic acid, and the mixture was warmed at 40° C. to 50° C. To the reaction mixture was added 20 mL of water, and the mixture was stirred at 50° C. for 2.5 hours and concentrated under house vacuum at 40° C. The residue was dissolved in dichloromethane/hexane, concentrated, and chromatographed on a 7×15 cm Biotage silica column eluted with 1:1:8 to 2.5:1:6.5 ethyl acetate/dichloromethane/hexane to give 3.2 g (66%) of the title compound as a yellow solid. A small portion that crystallized from the chromatography solvent was used for analysis. MS (APCI) (m+1)/z 359.1.

Analysis calculated for $C_{17}H_{19}N_5O_2S$: C, 56.97; H, 5.06; N, 15.63.

Found: C, 56.98; H, 4.95; N, 15.59.

EXAMPLE 7

3-(4-Diethylamino-butylamino)-7-(3,5-dimethoxy-phenyl)-5-ethyl-5H-pyrido[2,3-e]-1,2,4-triazin-6-one To 300 mg (0.84 mmol) of 7-(3,5-dimethoxy-phenyl)-5-ethyl-3-methylsulfanyl-5H-pyrido[2,3-e]-1,2,4-triazin-6-one was added 1.25 g (8.7 mmol) of N,N-diethylaminobutylamine. The reaction mixture was warmed at 70° C. for 1.5 hours and cooled to room temperature. A seed crystal was added to the solution, and it was set overnight. The resulting crystalline material was collected, washed with 1:1 diethyl ether/hexane and dried under house vacuum to give 318 mg (83%) of the title compound as pale yellow solid. Mp=120–121° C.(dec); when placed in a 119° C. melting point apparatus. MS (APCI) (m+1)/z 455.2.

Analysis calculated for $C_{24}H_{34}N_6O_3$: C, 63.41; H, 7.54; N, 18.49.

Found: C, 63.51; H, 7.53; N, 18.58.

EXAMPLE 8

7-(3,5-Dimethoxy-phenyl)-5-ethyl-3-(pyridin-4-ylamino)-5H-pyrido[2,3-e]-1,2,4-triazin-6-one A homogenious mixture of 1.8 g (5.0 mmol) of 7-(3,5-dimethoxy-phenyl)-5-ethyl-3-methylsulfanyl-5H-pyrido[2,3-e]-1,2,4-triazin-6-one and 3.3 g (35.2 mmol) of 4-aminopyridine was heated at 150° C. for 2 days in a sealed reaction vessel, during which time the sublimed 4-aminopyrdine was reintroduced to the reaction mixture. At the end of 2 days, the sublimed 4-aminopyridine was removed, and the remaining mixture was triturated under 1:9 methanol/chloroform at room temperature and filtered. The solid was suspended in 60 mL of hot chloroform while methanol was added to produce a near homogeneous solution that was filtered and set aside for 6 days. The crystals were collected, washed with chloroform, and dried under house vacuum to give 610 mg (30%) of the title compound as yellow platelets. Mp=316–318° C. (dec).

MS (APCI) (m+1)/z 405.1.

Analysis calculated for $C_{21}H_{20}N_6O_3$: C, 62.37; H, 4.98; N, 20.78.

Found: C, 62.10; H, 4.83; N, 20.59.

As noted above, the compounds of this invention are inhibitors of a variety of kinases, and accordingly, are useful in treating and preventing atherosclerosis, and other cell proliferative disorders like cancer. The compounds have low toxicity. The compounds have been evaluated in assay systems routinely utilized to measure inhibitory effect against kinase activity and have demonstrated inhibitory activity against a wide variety of kinases, especially the tyrosine kinases. The compounds can also be evaluated in the assays utilized to determine the activity against cyclin-dependent kinases and would be expected to demonstrate similar activities. A typical assay, for instance, measures inhibitory activity against the cyclin D dependent kinase 4 enzyme (cdk4/D). The cdk4 assay is carried out as follows.

Cyclin-Dependent Kinase 4 (cdk4) Assay

Enzyme assays for $IC_{50}$ determinations and kinetic evaluation are performed in 96 well filter plates (Millipore MADVN6550). The total volume is 0.1 mL containing a final concentration of 20 mM TRIS (tris[hydroxymethyl]-aminomethane), at pH 7.4, 50 mM NaCl, 1 mM dithiothreitol, 10 mM $MgCl_2$, 25 $\mu$M ATP containing 0.25 $\mu$Ci of [$^{32}$P]ATP, 20 ng of cdk4, 1 $\mu$g of retinoblastoma, and appropriate dilutions of a compound of the present invention. All components except the ATP are added to the wells, and the plate is placed on a plate mixer for 2 minutes. The reaction is started by adding [$^{32}$P]ATP and the plate is incubated at 25° C. for 15 minutes. The reaction is terminated by addition of 0.1 mL of 20% trichloroacetic acid (TCA). The plate is kept at 4° C. for at least 1 hour to allow the substrate to precipitate. The wells are then washed five times with 0.2 mL of 10% TCA and $^{32}$P incorporation is determined with a beta plate counter (Wallac Inc., Gaithersburg, Md.).

Cyclin-Dependent Kinase Assays (cdk2/cyclinE, cdk2/cyclinA, cdc2/cyclinB)

Enzyme assays for $IC_{50}$ determinations and kinetic evaluation were performed in a 96-well filter plate (Millipore MADVN6550) in a total volume of 0.1 mL of 20 mM TRIS (tris[hydroxymethyl]aminomethane), at pH 7.4, 50 mM NaCl, 1 mM dithiothreitol, 10 mM $MgCl_2$, 12 mM ATP containing 0.25 $\mu$Ci of [$^{32}$P]ATP, 20 ng of enzyme (either cdk2/cyclinE, cdk2/A, or cdc2/cyclinB), 1 $\mu$g retinoblastoma, and appropriate dilutions of the particular invention compound. All components except the ATP were added to the wells, and the plate was placed on a plate mixer for 2 minutes. The reaction was begun by addition of [$^{32}$P]ATP, and the plate was incubated at 25° C. for 15 minutes. The reaction was terminated by addition of 0.1 mL of 20% TCA. The plate was kept at 4° C. for at least 1 hour to allow the substrate to precipitate. The wells were then washed five times with 0.2 mL of 10% TCA and $^{32}$P incorporation determined with a beta plate counter (Wallac Inc., Gaithersburg, Md.).

The assays used to determine the activity against $cdk6/D_2$ and $cdk6/D_3$ enzymes were carried out in a manner similar to that described above for cdk4, by simply employing the appropriate cdk6 kinase enzyme.

The compounds of Formula I have shown good inhibitory activity against certain growth factor receptor tyrosine kinase enzymes, including those of fibroblast growth factor (FGF) and platelet derived growth factor (PDGF). The assays used to determine these activities were carried out as follows:

PDGF and FGF Receptor Tyrosine Kinase Assays

Full-length cDNAs for the mouse PDGF-β and human FGF-1 (flg) receptor tyrosine kinases were obtained from J. Escobedo and prepared as described in *J. Biol. Chem.*, 1991;262:1482–1487. PCR primers were designed to amplify a fragment of DNA that codes for the intracellular tyrosine kinase domain. The fragment was inserted into a baculovirus vector, cotransfected with AcMNPV DNA, and the recombinant virus isolated. SF9 insect cells were infected with the virus to overexpress the protein, and the cell lysate was used for the assay. Assays were performed in 96-well plates (100 µL/incubation/well), and conditions were optimized to measure the incorporation of $^{32}P$ from $\gamma^{32}P$-ATP into a glutamate-tyrosine co-polymer substrate. Briefly, to each well was added 82.5 µL of incubation buffer containing 25 mM Hepes (pH 7.0), 150 mM NaCl, 0.1% Triton X-100, 0.2 mM PMSF, 0.2 mM $Na_3VO_4$, 10 mM $MnCl_2$, and 750 µg/mL of Poly (4:1) glutamate-tyrosine followed by 2.5 µL of inhibitor and 5 µL of enzyme lysate (7.5 µg/µL FGF-TK or 6.0 µg/µL PDGF-TK) to initiate the reaction. Following a 10 minute incubation at 25° C., 10 mL of $\gamma^{32}P$-ATP (0.4 µCi plus 50 µM ATP) was added to each well, and samples were incubated for an additional 10 minutes at 25° C. The reaction was terminated by the addition of 100 µL of 30% trichloroacetic acid (TCA) containing 20 mM sodium pyrophosphate and precipitation of material onto glass fiber mats (Wallac). Filters were washed three times with 15% TCA containing 100 mM sodium pyrophosphate, and the radioactivity retained on the filters counted in a Wallac 1250 Betaplate reader. Nonspecific activity was defined as radioactivity retained on the filters following incubation of samples with buffer alone (no enzyme). Specific enzymatic activity (enzyme plus buffer) was defined as total activity minus nonspecific activity. The concentration of a compound that inhibited specific activity by 50% ($IC_{50}$) was determined based on the inhibition curve.

The Src (the transforming gene of the Rous sarcoma retrovirus) family of non-receptor protein kinases, which all contain a SH2 domain, are involved in a number of cellular signaling pathways. For example, Src is involved in growth factor receptor signaling; integrin-mediated signaling; T- and B-cell activation and osteoclast activation. It is known that the Src SH2 domain binds to several key receptor and non-receptor tyrosine kinases such as tyrosine kinases containing receptors for PDGF, EGF, HER2/Neu (an oncogene form of EGF), FGF, focal adhesion kinase, p130 protein, and p68 protein. In addition, pp60c-Src has been shown to be involved in the regulation of DNA synthesis, mitosis, and other cellular activities.

Thus, it would be useful to have compounds that inhibit the binding of proteins containing an SH2 domain to cognate phosphorylated proteins, as the inhibition of binding of proteins containing an SH2 domain to cognate phosphorylated proteins can be used to treat proliferative diseases such as cancer, osteoporosis, inflammation, allergy, restenosis, and cardiovascular disease, which all rely on signal transduction involving proteins that contain an SH2 domain that binds to phosphorylated proteins during the cellular signaling process.

The assay used to determine the inhibitory activity of the inventive compounds against cellular Src protein kinase (c-Src) is carried out as follows:

c-Src kinase is purified from baculovirus infected insect cell lysates using an antipeptide monoclonal antibody directed against the N-terminal amino acids (amino acids 2–17) of c-Src. The antibody, covalently linked to 0.65 µm latex beads, is added to a suspension of insect cell lysis buffer comprised of 150 mM NaCl, 50 mM Tris pH 7.5, 1 mM DTT, 1% NP-40, 2 mM EGTA, 1 mM sodium vanadate, 1 mM PMSF, 1 µg/mL each of leupeptin, pepstatin, and aprotinin. Insect cell lysate containing c-Src protein is incubated with these beads for 3 to 4 hours at 4° C. with rotation. At the end of the lysate incubation, the beads are rinsed three times in lysis buffer, resuspended in lysis buffer containing 10% glycerol, and frozen. These latex beads are thawed, rinsed three times in assay buffer (40 mM Tris, pH 7.5, 5 mM µgCl$_2$) and suspended in the same buffer. In a Millipore 96-well plate with a 0.65 µm polyvinylidine membrane bottom are added the reaction components: 10 µL c-Src beads, 10 µL of 2.5 mg/mL poly GluTyr substrate, 5 µM ATP containing 0.2 µCi labeled $^{32}P$-ATP, 5 µL DMSO containing inhibitors or as a solvent control, and buffer to make the final volume 125 µL. The reaction is started at room temperature by addition of the ATP and quenched 10 minutes later by the addition of 125 µL of 30% TCA, 0.1 M sodium pyrophosphate for 5 minutes on ice. The plate is then filtered and the wells washed with two 250 mL aliquots of 15% TCA, 0.1 M pyrophosphate. The filters are then punched, counted in a liquid scintillation counter, and the data examined for inhibitory activity in comparison to a known inhibitor such as erbstatin. The method is also described in *J. Med. Chem.*, 1994;37:598–609.

The inhibition activity of the compounds in Examples 7 and 8 were also evaluated using the Dissociated Enhanced Lanthanide Fluoroimmuno Assay (DELFIA) (Frank Loganzo and Carolyn Harady. A sensitive, time-resolved fluorometric assay for the detection of inhibitors of phosphotyrosine kinases. *American Biotechnology Laboratory*, December 1998). DELFIA plates (EG&G Wallac, Gaithersburg, Md.) were coated overnight with Poly Glu Tyr (4:1) (Sigma, St. Louis, Mo.) overnight at room temperature, washed (DELFIA wash reagent, EG&G Wallac), and spotted with 1 µL inhibitor dilution or DMSO carrier control per well. In some cases, kinase was autophosphorylated prior to analysis by incubating 45 minutes at 4° C. in the presence of 4 mM ATP and 25 mM MgCl$_2$. A typical 100 µL kinase assay reaction contained 20 mM Tris (pH 7.5), 20 mM MgCl$_2$, 50 mM NaCl, 5 mM DTT, 200 µM ATP, and protease inhibitors (Mini EDTA-free protease inhibitor cocktail tablets, Boehringer Mannheim, Indianapolis, Ind.), 40 µM ATP, and an appropriate concentration of inhibitor. The reaction was allowed to continue for 30 minutes at room temperature. Plates were washed, blocked 30 minutes at room temperature (0.5% bovine serum albumin in DELFIA Assay Buffer, EG&G Wallac), and washed. One hundred microliter europium-conjugated antiphosphotyrosine antibody in DELFIA Assay Buffer was added to each well. Plates were incubated for 1 hour and decanted. One hundred microliter DELFIA Enhancement Solution (EG&G Wallac) was added and time-resolved fluorescence of the reactions determined using a VICTOR2 1420 multilable counter (EG&G Wallac). Compounds were tested from 10 through 0.0001 µM. c-Src (Upstate Biotechnology, Lake Placid, N.Y.) was used at 3 units per reaction. The kinase domains from FGFR-1, VEGFR-2, Lck, and PDGF were purified from baculoviral vectors expression systems and were used in the assays at 20 nM. Results of the inhibition activity of the compounds in Examples 7 and 8 are shown in Table 1.

| Example | FGFR ($IC_{50}$ = µM) | (VEGF-2) ($IC_{50}$ = µM) | PDGF ($IC_{50}$ = µM) | Lck (Ki = µM) | c-Src ($IC_{50}$ = µM) |
|---|---|---|---|---|---|
| 7 | 6.04 | | >50 | | 10.57 |
| 8 | 1.22 | 0.35 | >50 | >4 | >4 |

The compounds of Formula I are useful for treating cell proliferative disorders concerning angiogenesis and have been evaluated in a human umbilical vein endothelial cell in vitro assay. The assay described below is used to determine the anti-proliferative effects of the invention compounds on human umbilical vein endothelial cells.

Cellular Proliferation Assays

Human umbilical vein endothelial cells (HUVEC) (Clonetics, Palo Alto, Calif.) were seeded at 2000 cells per well in growth medium containing 2% serum (EGM, Clonetics) and allowed to attach overnight (37° C., 5% $CO_2$, 100% humidity). C6 rat glioma cells (ATCC) were seeded at 600 cells per well and incubated in F10 medium (GIBCO, Gaithersburg, Md.) supplemented with 15% horse serum, 2.5% fetal bovine serum, and 1 mM glutamnine. A90 human ovarian cells (Dr. Kent Crickard, SUNY/AB Medical School) were seeded at 600 cells per well in RPMI 1640 (GIBCO) plus 10% fetal bovine serum. Plates were incubated overnight (37° C., 5% $CO_2$, 100% humidity) to allow the cells to attach. Test compound dilutions were added to the appropriate wells, and the incubation was continued for 4 additional days. Monolayers were fixed in 10% trichloroacetic acid (30 minutes at 4° C.), washed with distilled water, and stained with Sulphorhodamine B (0.075% in 1% acetic acid). Plates were washed in 1% acetic acid, and the bound dye was solubilized in 100 μL unbuffered TRIS base. Absorbance was measured at 540 nm using a reference filter wavelength of 630 nm. Inhibitor potency ($IC_{50}$) was determined from the absorbed measurements. Sulphorhodamine B and TRIS are from Sigma Chemical Company. Acetic acid and trichloroacetic acid are from Mallinckrodt AR.

The invention compounds can be formulated in conventional manners to provide convenient dosage forms for delivery to mammals by various routes, including oral, parenteral (i.e., subcutaneous, intravenous, and intramuscular), transdermal, e.g., slow release skin patch or cream, as well as by slow release delivery devices such as osmotic pumps, suppositories, and buccal seals. The following examples further illustrate how the compounds are readily formulated.

EXAMPLE 9

50 mg Tablet Formulation

| Per Tablet | | Per 10,000 Tablets |
|---|---|---|
| 0.050 g | 7-(3,5-Dimethoxy-phenyl)-5-ethyl-3-(pyridin-4-ylamino)-5H-pyrido[2,3-e]-1,2,4-triazin-6-one | 500 g |
| 0.080 g | lactose | 800 g |
| 0.010 g | corn starch (for mix) | 100 g |
| 0.008 g | corn starch (for paste) | 80 g |
| 0.148 g | | 1480 g |
| 0.002 g | magnesium stearate (1%) | 20 g |
| 0.150 g | | 1500 g |

The pyridotriazine, lactose, and corn starch (for mix) are blended to uniformity. The corn starch (for paste) is suspended in 600 mL of water and heated with stirring to form a paste. This paste is used to granulate the mixed powders. The wet granules are passed through a No. 8 hand screen and dried at 80° C. The dry granules are then passed through a No. 16 screen. The mixture is lubricated with 1% magnesium stearate and compressed into tablets in a conventional tableting machine. The tablets, as well as all invention compounds, are useful for treating cancers such as breast, prostate, lung, ovarian, colon, pancreatic, melanoma, esophageal, brain, Kaposi's sarcoma, and lymphomas and smooth muscle proliferation. Particular concerns to be treated include small-cell lung carcinoma, low-grade human bladder carcinoma, and human colorectal cancer.

EXAMPLE 10

Preparation of Oral Suspension

| Ingredient | Amount |
|---|---|
| 7-(3,5-Dimethoxy-phenyl)-5-ethyl-3-(pyridin-4-ylamino)-5H-pyrido[2,3-e]-1,2,4-triazin-6-one | 500 mg |
| Sorbitol solution (70% N.F.) | 40 mL |
| Sodium benzoate | 150 mg |
| Saccharin | 10 mg |
| Cherry flavor | 50 mg |
| Distilled water qs | 100 mL |

The sorbitol solution is added to 40 mL of distilled water, and the pyridotriazine is suspended therein. The saccharin, sodium benzoate, and flavoring are added and dissolved. The volume is adjusted to 100 mL with distilled water. Each milliliter of syrup contains 5 mg of invention compound.

EXAMPLE 11

Preparation of Parenteral Solution

In a solution of 700 mL of propylene glycol and 200 mL of water for injection is suspended 20.0 g 7-(3,5-dimethoxy-phenyl)-5-ethyl-3-(pyridin-4-ylamino)-5H-pyrido[2,3-e]-1,2,4-triazin-6-one with stirring. After suspension is complete, the pH is adjusted to 5.5 with hydrochloric acid, and the volume is made up to 1000 mL with water for injection. The formulation is sterilized, filled into 5.0 mL ampoules, each containing 2.0 mL (representing 40 mg of invention compound) and sealed under nitrogen.

EXAMPLE 12

Suppositories

A mixture of 400 mg of 7-(3,5-dimethoxy-phenyl)-5-ethyl-3-(pyridin-4-ylamino)-5H-pyrido[2,3-e]-1,2,4-triazin-6-one, and 600 mg of theobroma oil is stirred at 60° C. to uniformity. The mixture is cooled and allowed to harden in a tapered mold to provide a 1 g suppository.

EXAMPLE 13

Slow Release Formulation

Five hundred milligrams of 7-(3,5-dimethoxy-phenyl)-5-ethyl-3-(pyridin-4-ylamino)-5H-pyrido[2,3-e]-1,2,4-triazin-6-one is converted to a hydrochloride salt and placed into an Oros osmotic pump for controlled release for treatment of atherosclerosis.

EXAMPLE 14

Skin Patch Formulation

Fifty milligrams of 7-(3,5-dimethoxy-phenyl)-5-ethyl-3-(pyridin-4-ylamino)-5H-pyrido[2,3-e]-1,2,4-triazin-6-one is admixed with 50 mg of propylene glycol monolaurate in a polydimethylsiloxane adhesive. The mixture is layered onto an elastic film made with an adhesive formulation of polybutene, polyisobutylene, and propylene glycol monolaurate. The layers are placed between 2 layers of polyurethane film. A release liner is attached to the adhesive surface, and is removed prior to application to a skin surface. The propylene glycol monolaurate serves as a permeation-enhancing agent.

Other Embodiments

From the above disclosure and examples, and from the claims below, the essential features of the invention are readily apparent. The scope of the invention also encompasses various modifications and adaptations within the knowledge of a person of ordinary skill. Examples include a disclosed compound modified by addition or removal of a protecting group, or an ester, pharmaceutical salt, hydrate, acid, or amide of a disclosed compound. Publications cited herein are hereby incorporated by reference in their entirety.

What is claimed is:

1. A compound of Formula I

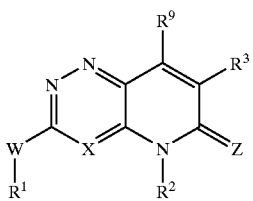

or the pharmaceutically acceptable salts thereof, wherein:

W is NH, S, SO, or $SO_2$;

X is N;

Z is O, S, or $NR^{10}$;

Each of $R^1$, $R^2$, and $R^{10}$ are independently selected from the group consisting of H, $(CH_2)_nAr$, $COR^4$, $(CH_2)_n$ $C_3$–$C_5$ heteroaryl, $(CH_2)_n$ $C_3$–$C_6$ heterocyclyl, $C_1$–$C_{10}$ alkyl, $C_3$–$C_{10}$ cycloalkyl, $C_2$–$C_{10}$ alkenyl, and $C_2$–$C_{10}$ alkynyl, wherein n is 0–6 and the $(CH_2)_nAr$, $(CH_2)_n$ heteroaryl, heterocyclyl, alkyl, cycloalkyl, alkenyl, and alkynyl groups are optionally substituted by up to 5 groups selected from $NR^5R^6$, $N(O)R^5R^6$, $NR^5R^6R^7Y$, $C_1$–$C_4$ alkyl, phenyl, substituted phenyl, $(CH_2)_n$ heteroaryl, hydroxy, $C_1$–$C_4$ alkoxy, phenoxy, thiol, $C_1$–$C_4$ thioalkyl, halo, $COR^5$, $CO_2R^5$, $CONR^5R^6$, $SO_2NR^5R^6$, $SO_2R^5$, $SO_3R^5$, $PO_3R^5$, $C_1$–$C_5$ aldehyde, nitrile, nitro, $C_3$–$C_6$ heteroaryloxy, $T(CH_2)_mQR^4$,

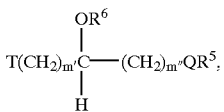

$C(O)T(CH_2)_mQR^5$, $NHC(O)T(CH_2)_mQR^5$, $T(CH_2)_mC(O)NR^5NR^6$, and $T(CH_2)_mCO_2R^5$, wherein each of m, m' and m" is independently 1–6, T is O, S, $NR^7$, $N(O)R^7$, $NR^7R^8Y$, or $CR^7R^{11}$, and Q is O, S, $NR^{11}$, $N(O)R^{11}$, or $NR^{11}R^8Y$;

$R^3$ and $R^9$ are each OH, $NR^{12}R^{13}$, $COOR^{12}$, $OR^{12}$, $CONR^{12}R^{13}$, $(CH^2)_nCOR^{12}$, $(CH_2)_nCOOR^{12}$, halo, $SO_2NR^{12}R^{13}$, $SO_3R^{12}$, $PO_3R^{12}$, $T'(CH_2)_mQ'R^4$,

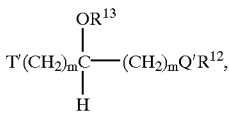

or as defined above for $R^2$, wherein T' and Q' are as defined above for T and Q, respectively;

$R^4$, $R^5$, $R^6$, $R^7$, $R_{11}$, $R^{12}$, $R^{13}$, $R^{14}$, and $R^{15}$ are each independently selected from the group consisting of hydrogen, $C_1$–$C_6$ alkyl, substituted $C_1$–$C_6$ alkyl, $C_2$–$C_6$ alkenyl, $C_2$–$C_6$ alkynyl, $N(C_1$–$C_6alkyl)_{1\,or\,2}$, $(CH_2)_nAr$, $C_3$–$C_{10}$ cycloalkyl, $C_3$–$C_6$ heterocyclyl, and $C_3$–$C_6$ heteroaryl, or $R^5$ and $R^6$, or $R^7$ and $R^8$, or $R^{12}$ and $R^{13}$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, sulfur, and substituted sulfur; or when $R^5$ and $R^6$, or $R^7$ and $R^8$, or $R^{12}$ and $R^{13}$ together with the nitrogen to which they are attached form a ring, said ring is optionally substituted by 1 to 3 groups selected from $C_1$–$C_3$ alkyl, OH, $OR^{14}$, $NR^{14}R^{15}$, $(CH_2)_m$ $OR^{14}$, $(CH_2)_mNR^{14}R^{15}$, $T"$—$(CH_2)_mQ"R^{14}$, $CO$—$T"$—$(CH_2)_mQ"R^{14}$, $NH(CO)T"(CH_2)_mQ"R^{14}$, $T"$—$(CH_2)_mCO_2R^{14}$, or $T"(CH_2)_mCONR^{14}R^{15}$; wherein T" and Q" are as defined above for T and Q;

$R^8$ is $C_1$–$C_6$ alkyl or $C_3$–$C_6$ cycloalkyl; and

Y is a halo counter-ion.

2. A compound of claim 1 wherein W is NH and X is N.

3. A compound of claim 1 or 2 wherein Z is $NR^{10}$.

4. A compound of claim 1 or 2 wherein Z is O.

5. A compound of claim 1 or 2, wherein $R^2$ is hydrogen.

6. A compound of claim 1 or 2, wherein $R^1$ is cycloalkyl, substituted cycloalkyl, alkyl, substituted alkyl, phenyl, substituted phenyl, pyridyl, or substituted pyridyl.

7. A compound of claim 1 or 2, wherein $R^2$ is alkyl, substituted alkyl, cycloalkyl, or substituted cycloalkyl.

8. A compound of claim 1 or 2, wherein $R^9$ is hydrogen or alkyl.

9. A compound of claim 1 or 2, wherein $R^3$ is hydrogen, cycloalkyl, substituted cycloalkyl, alkyl, substituted alkyl, phenyl, substituted phenyl, pyridyl or substituted pyridyl.

10. A compound of claim 1 wherein W is S, SO, or $SO_2$.

11. A pharmaceutical composition comprising a compound of Formula I according to claim 1 and a pharmaceutically acceptable carrier.

12. A compound of claim 1 selected from:

5-Cyclopentyl-3-(pyridin-4-ylamino)-5H-pyrido[2,3-e]-1,2,4-triazin-6-one;

5-Cyclopentyl-8-methyl-3-(pyridin-4-ylamino)-5H-pyrido[2,3-e]-1,2,4-triazin-6-one;

4-(5-Cyclopentyl-6-oxo-5,6-dihydro-pyrido[2,3-e]-1,2,4-triazin-3-ylamino)-benzenesulfonamide;

4-(5-Cyclopentyl-8-methyl-6-oxo-5,6-dihydro-pyrido[2,3-e]-1,2,4-triazin-3-ylamino)-benzenesulfonamide;

5-Cyclopentyl-3-(4-piperazin-1-yl-phenylamino)-5H-pyrido[2,3-e]-1,2,4-triazin-6-one;

4-[4-(5-Cyclopentyl-6-oxo-5,6-dihydro-pyrido[2,3-e]-1,2,4-triazin-3-ylamino)-phenyl]-piperazine-1-carboxylic acid amide;

5-Cyclopentyl-8-methyl-3-(4-piperazin-1-yl-phenylamino)-5H-pyrido[2,3-e]-1,2,4-triazin-6-one;

4-[4-(5-Cyclopentyl-8-methyl-6-oxo-5,6-dihydro-pyrido[2,3-e]-1,2,4-triazin-3-ylamino)-phenyl]-piperazine-1-carboxylic acid amide;

5-Cyclopentyl-3-[4-(3,5-dimethyl-piperazin-1-yl)-phenylamino]-5H-pyrido[2,3-e]-1,2,4-triazin-6-one;

4-[4-(5-Cyclopentyl-6-oxo-5,6-dihydro-pyrido[2,3-e]-1,2,4-triazin-3-ylamino)-phenyl]-2,6-dimethyl-piperazine-1-carboxylic acid amide;

5-Cyclopentyl-3-[4-(3,5-dimethyl-piperazin-1-yl)-phenylamino]-8-methyl-5H-pyrido[2,3-e]-1,2,4-triazin-6-one;

4-[4-(5-Cyclopentyl-8-methyl-6-oxo-5,6-dihydro-pyrido[2,3-e]-1,2,4-triazin-3-ylamino)-phenyl]-2,6-dimethyl-piperazine-1-carboxylic acid amide;

7-(2-Chloro-3,5-dimethoxy-phenyl)-5-ethyl-3-(pyridin-4-ylamino)-5H-pyrido[2,3-e]-1,2,4-triazin-6-one;
7-(2,6-Dichloro-3,5-dimethoxy-phenyl)-5-ethyl-3-(pyridin-4-ylamino)-5H-pyrido[2,3-e]-1,2,4-triazin-6-one;
7-(3,5-Dimethoxy-2-methyl-phenyl)-5-ethyl-3-(pyridin-4-ylamino)-5H-pyrido[2,3-e]-1,2,4-triazin-6-one;
7-(3,5-Dimethoxy-phenyl)-5-ethyl-3-(pyridin-4-ylamino)-5H-pyrido[2,3-e]-1,2,4-triazin-6-one;
7-(3,5-Dimethoxy-2,6-dimethyl-phenyl)-5-ethyl-3-(pyridin-4-ylamino)-5H-pyrido[2,3-e]-1,2,4-triazin-6-one;
5-Cyclopentyl-7-(3,5-dimethoxy-phenyl)-3-(pyridin-4-ylamino)-5H-pyrido[2,3-e]-1,2,4-triazin-6-one;
7-(2-Chloro-3,5-dimethoxy-phenyl)-5-cyclopentyl-3-(pyridin-4-ylamino)-5H-pyrido[2,3-e]-1,2,4-triazin-6-one;
5-Cyclopentyl-7-(2,6-dichloro-3,5-dimethoxy-phenyl)-3-(pyridin-4-ylamino)-5H-pyrido[2,3-e]-1,2,4-triazin-6-one;
5-Cyclopentyl-7-(3,5-dimethoxy-2-methyl-phenyl)-3-(pyridin-4-ylamino)-5H-pyrido[2,3-e]-1,2,4-triazin-6-one;
5-Cyclopentyl-7-(3,5-dimethoxy-2,6-dimethyl-phenyl)-3-(pyridin-4-ylamino)-5H-pyrido[2,3-e]-1,2,4-triazin-6-one;
7-(2,6-Dimethoxy-pyridin-4-yl)-5-ethyl-3-(pyridin-4-ylamino)-5H-pyrido[2,3-e]-1,2,4-triazin-6-one;
7-(3-Chloro-2,6-dimethoxy-pyridin-4-yl)-5-ethyl-3-(pyridin-4-ylamino)-5H-pyrido[2,3-e]-1,2,4-triazin-6-one;
7-(3,5-Dichloro-2,6-dimethoxy-pyridin-4-yl)-5-ethyl-3-(pyridin-4-ylamino)-5H-pyrido[2,3-e]-1,2,4-triazin-6-one;
5-Cyclopentyl-7-(2,6-dimethoxy-pyridin-4-yl)-3-(pyridin-4-ylamino)-5H-pyrido[2,3-e]-1,2,4-triazin-6-one;
7-(3-Chloro-2,6-dimethoxy-pyridin-4-yl)-5-cyclopentyl-3-(pyridin-4-ylamino)-5H-pyrido[2,3-e]-1,2,4-triazin-6-one;
5-Cyclopentyl-7-(3,5-dichloro-2,6-dimethoxy-pyridin-4-yl)-3-(pyridin-4-ylamino)-5H-pyrido[2,3-e]-1,2,4-triazin-6-one;
7-(2-Chloro-3,5-dimethoxy-phenyl)-3-[4-(2-diethylamino-ethoxy)-phenylamino]-5-ethyl-5H-pyrido[2,3-e]-1,2,4-triazin-6-one;
7-(2,6-Dichloro-3,5-dimethoxy-phenyl)-3-[4-(2-diethylamino-ethoxy)-phenylamino]-5-ethyl-5H-pyrido[2,3-e]-1,2,4-triazin-6-one;
3-[4-(2-Diethylamino-ethoxy)-phenylamino]-7-(3,5-dimethoxy-2-methyl-phenyl)-5-ethyl-5H-pyrido[2,3-e]-1,2,4-triazin-6-one;
3-(4-Diethylamino-butylamino)-7-(3,5-dimethoxy-phenyl)-5-ethyl-5H-pyrido[2,3-e]-1,2,4-triazin-6-one;
3-[4-(2-Diethylamino-ethoxy)-phenylamino]-7-(3,5-dimethoxy-2,6-dimethyl-phenyl)-5-ethyl-5H-pyrido[2,3-e]-1,2,4-triazin-6-one;
5-Cyclopentyl-3-[4-(2-diethylamino-ethoxy)-phenylamino]-7-(3,5-dimethoxy-phenyl)-5H-pyrido[2,3-e]-1,2,4-triazin-6-one;
7-(2-Chloro-3,5-dimethoxy-phenyl)-5-cyclopentyl-3-[4-(2-diethylamino-ethoxy)-phenylamino]-5H-pyrido[2,3-e]-1,2,4-triazin-6-one;
5-Cyclopentyl-7-(2,6-dichloro-3,5-dimethoxy-phenyl)-3-[4-(2-diethylamino-ethoxy)-phenylamino]-5H-pyrido[2,3-e]-1,2,4-triazin-6-one;
5-Cyclopentyl-3-[4-(2-diethylamino-ethoxy)-phenylamino]-7-(3,5-dimethoxy-2-methyl-phenyl)-5H-pyrido[2,3-e]-1,2,4-triazin-6-one;
5-Cyclopentyl-3-[4-(2-diethylamino-ethoxy)-phenylamino]-7-(3,5-dimethoxy-2,6-dimethyl-phenyl)-5H-pyrido[2,3-e]-1,2,4-triazin-6-one;
3-[4-(2-Diethylamino-ethoxy)-phenylamino]-7-(2,6-dimethoxy-pyridin-4-yl)-5-ethyl-5H-pyrido[2,3-e]-1,2,4-triazin-6-one;
7-(3-Chloro-2,6-dimethoxy-pyridin-4-yl)-3-[4-(2-diethylamino-ethoxy)-phenylamino]-5-ethyl-5H-pyrido[2,3-e]-1,2,4-triazin-6-one;
7-(3,5-Dichloro-2,6-dimethoxy-pyridin-4-yl)-3-[4-(2-diethylamino-ethoxy)-phenylamino]-5-ethyl-5H-pyrido[2,3-e]-1,2,4-triazin-6-one;
7-(2-Chloro-3,5-dimethoxy-phenyl)-3-(4-diethylamino-butylamino)-5-ethyl-5H-pyrido[2,3-e]-1,2,4-triazin-6-one;
7-(2,6-Dichloro-3,5-dimethoxy-phenyl)-3-(4-diethylamino-butylamino)-5-ethyl-5H-pyrido[2,3-e]-1,2,4-triazin-6-one;
3-(4-Diethylamino-butylamino)-7-(3,5-dimethoxy-2-methyl-phenyl)-5-ethyl-5H-pyrido[2,3-e]-1,2,4-triazin-6-one;
3-(4-Diethylamino-butylamino)-7-(3,5-dimethoxy-2,6-dimethyl-phenyl)-5-ethyl-5H-pyrido[2,3-e]-1,2,4-triazin-6-one;
5-Cyclopentyl-3-(4-diethylamino-butylamino)-7-(3,5-dimethoxy-phenyl)-5H-pyrido[2,3-e]-1,2,4-triazin-6-one;
7-(2-Chloro-3,5-dimethoxy-phenyl)-5-cyclopentyl-3-(4-diethylamino-butylamino)-5H-pyrido[2,3-e]-1,2,4-triazin-6-one;
5-Cyclopentyl-7-(2,6-dichloro-3,5-dimethoxy-phenyl)-3-(4-diethylamino-butylamino)-5H-pyrido[2,3-e]-1,2,4-triazin-6-one;
5-Cyclopentyl-3-(4-diethylamino-butylamino)-7-(3,5-dimethoxy-2-methyl-phenyl)-5H-pyrido[2,3-e]-1,2,4-triazin-6-one;
5-Cyclopentyl-3-(4-diethylamino-butylamino)-7-(3,5-dimethoxy-2,6-dimethyl-phenyl)-5H-pyrido[2,3-e]-1,2,4-triazin-6-one;
3-(4-Diethylamino-butylamino)-7-(2,6-dimethoxy-pyridin-4-yl)-5-ethyl-5H-pyrido[2,3-e]-1,2,4-triazin-6-one;
7-(3-Chloro-2,6-dimethoxy-pyridin-4-yl)-3-(4-diethylamino-butylamino)-5-ethyl-5H-pyrido[2,3-e]-1,2,4-triazin-6-one;
7-(3,5-Dichloro-2,6-dimethoxy-pyridin-4-yl)-3-(4-diethylamino-butylamino)-5-ethyl-5H-pyrido[2,3-e]-1,2,4-triazin-6-one;
5-Cyclopentyl-3-(4-diethylamino-butylamino)-7-(2,6-dimethoxy-pyridin-4-yl)-5H-pyrido[2,3-e]-1,2,4-triazin-6-one;
7-(3-Chloro-2,6-dimethoxy-pyridin-4-yl)-5-cyclopentyl-3-(4-diethylamino-butylamino)-5H-pyrido[2,3-e]-1,2,4-triazin-6-one;
5-Cyclopentyl-7-(3,5-dichloro-2,6-dimethoxy-pyridin-4-yl)-3-(4-diethylamino-butylamino)-5H-pyrido[2,3-e]-1,2,4-triazin-6-one;
7-Acetyl-5-cyclopentyl-8-methyl-3-(4-piperazin-1-yl-phenylamino)-5H-pyrido[2,3-e][1,2,4]triazin-6-one;
5-Cyclopentyl-8-methyl-6-oxo-3-(4-piperazin-1-yl-phenylamino)-5,6-dihydro-pyrido[2,3-e][1,2,4]triazine-7-carboxylic acid ethyl ester;
7-Acetyl-5-cyclopentyl-3-(4-piperazin-1-yl-phenylamino)-5H-pyrido[2,3-e][1,2,4]triazin-6-one;
7-Benzyl-5-cyclopentyl-3-(4-piperazin-1-yl-phenylamino)-5H-pyrido[2,3-e][1,2,4]triazin-6-one;
7-Benzyl-5-cyclopentyl-3-(4-piperazin-1-yl-cyclohexylamino)-5H-pyrido[2,3-e][1,2,4]triazin-6-one;
7-Benzyl-5-cyclopentyl-3-(4-dimethylamino-cyclohexylamino)-5H-pyrido[2,3-e][1,2,4]triazin-6-one;
7-Bromo-5-cyclopentyl-3-(4-piperazin-1-yl-phenylamino)-5H-pyrido[2,3-e][1,2,4]triazin-6-one;

7-Bromo-5-cyclopentyl-8-methyl-3-(4-piperazin-1-yl-phenylamino)-5H-pyrido[2,3-e][1,2,4]triazin-6-one;

7-Benzyl-5-cyclopentyl-3-(1-propyl-piperidin-4-ylamino)-5H-pyrido[2,3-e][1,2,4]triazin-6-one;

7-Benzyloxy-5-cyclopentyl-3-(4-piperazin-1-yl-phenylamino)-5H-pyrido[2,3-e][1,2,4]triazin-6-one;

5-Cyclopentyl-7-ethyl-3-(4-piperazin-1-yl-phenylamino)-5H-pyrido[2,3-e][1,2,4]triazin-6-one;

5-Cyclopentyl-3-(4-piperazin-1-yl-phenylamino)-7-propoxy-5H-pyrido[2,3-e][1,2,4]triazin-6-one;

5-Cyclopentyl-3-(4-piperazin-1-yl-phenylamino)-7-o-tolylamino-5H-pyrido[2,3-e][1,2,4]triazin-6-one;

5-Cyclopentyl-7-(4-methoxy-phenylamino)-3-(4-piperazin-1-yl-phenylamino)-5H-pyrido[2,3-e][1,2,4]triazin-6-one;

5-Cyclopentyl-7-(2-ethoxy-ethoxy)-3-(4-piperazin-1-yl-phenylamino)-5H-pyrido[2,3-e][1,2,4]triazin-6-one;

7-(3,5-Dimethoxy-phenyl)-5-ethyl-3-(pyridin-4-ylamino)-5H-pyrido[2,3-e]-1,2,4-triazin-6-one; and 3-(4-Diethylamino-butylamino)-7-(3,5-dimethoxy-phenyl)-5-ethyl-5H-pyrido[2,3-e]-1,2,4-triazin-6-one.

13. A compound of claim 3 wherein $R^2$ is hydrogen.

14. A compound of claim 3 wherein $R^1$ is cycloalkyl, substituted cycloalkyl, alkyl, substituted alkyl, phenyl, substituted phenyl, pyridyl, or substituted pyridyl.

15. A compound of claim 4 wherein $R^1$ is cycloalkyl, substituted cycloalkyl, alkyl, substituted alkyl, phenyl, substituted phenyl, pyridyl, or substituted pyridyl.

16. A compound of claim 5 wherein $R^1$ is cycloalkyl, substituted cycloalkyl, alkyl, substituted alkyl, phenyl, substituted phenyl, pyridyl, or substituted pyridyl.

17. A compound of claim 4 wherein $R^2$ is alkyl, substituted alkyl, cycloalkyl, or substituted cycloalkyl.

18. A compound of claim 3 wherein $R^9$ is hydrogen or alkyl.

19. A compound of claim 4 wherein $R^9$ is hydrogen or alkyl.

20. A compound of claim 5 wherein $R^9$ is hydrogen or alkyl.

21. A compound of claim 3 wherein $R^3$ is hydrogen, cycloalkyl, substituted cycloalkyl, alkyl, substituted alkyl, phenyl, substituted phenyl, pyridyl or substituted pyridyl.

22. A compound of claim 4 wherein $R^3$ is hydrogen, cycloalkyl, substituted cycloalkyl, alkyl, substituted alkyl, phenyl, substituted phenyl, pyridyl.

23. A compound of claim 5 wherein $R^3$ is hydrogen, cycloalkyl, substituted cycloalkyl, alkyl, substituted alkyl, phenyl, substituted phenyl, pyridyl or substituted pyridyl.

* * * * *